US012758477B2

(12) United States Patent
Milczek et al.

(10) Patent No.: US 12,758,477 B2
(45) Date of Patent: *Oct. 13, 2026

(54) SUNSCREEN COMPOSITIONS

(71) Applicant: Curie Co. Inc., New York, NY (US)

(72) Inventors: Erika M. Milczek, New York, NY (US); William Shindel, New York, NY (US); Zsolt Szabados, New York, NY (US)

(73) Assignee: Curie Co. Inc., New York, NY (US)

( * ) Notice: Subject to any disclaimer, the term of this patent is extended or adjusted under 35 U.S.C. 154(b) by 909 days.

This patent is subject to a terminal disclaimer.

(21) Appl. No.: 17/524,222

(22) Filed: Nov. 11, 2021

(65) Prior Publication Data

US 2022/0160601 A1 May 26, 2022

Related U.S. Application Data

(63) Continuation-in-part of application No. PCT/US2021/032217, filed on May 13, 2021.

(60) Provisional application No. 63/074,288, filed on Sep. 3, 2020, provisional application No. 63/024,398, filed on May 13, 2020.

(51) Int. Cl.

| | |
|---|---|
| ***A61K 8/40*** | (2006.01) |
| ***A61K 8/41*** | (2006.01) |
| ***A61K 8/44*** | (2006.01) |
| ***A61K 8/46*** | (2006.01) |
| ***A61K 8/64*** | (2006.01) |
| ***A61K 8/66*** | (2006.01) |
| ***A61K 8/891*** | (2006.01) |
| ***A61Q 17/04*** | (2006.01) |
| ***C12N 9/06*** | (2006.01) |
| ***C12N 9/10*** | (2006.01) |

(52) U.S. Cl.

CPC .................. *A61K 8/40* (2013.01); *A61K 8/41* (2013.01); *A61K 8/445* (2013.01); *A61K 8/466* (2013.01); *A61K 8/64* (2013.01); *A61K 8/66* (2013.01); *A61K 8/891* (2013.01); *A61Q 17/04* (2013.01); *C12N 9/0022* (2013.01); *C12N 9/1022* (2013.01); *C12Y 203/02013* (2013.01); *A61K 2800/26* (2013.01)

(58) Field of Classification Search

CPC .......... A61K 8/40; A61K 8/445; A61K 8/466; A61K 8/64; A61K 8/66; A61K 8/891; A61Q 17/04; C12N 9/0022; C12N 9/1022; C12Y 203/02013

See application file for complete search history.

(56) References Cited

U.S. PATENT DOCUMENTS

| | | | |
|---|---|---|---|
| 6,069,170 | A | 5/2000 | Bringhen et al. |
| 6,488,915 | B1 | 12/2002 | Heidenfelder et al. |
| 2005/0268405 | A1 | 12/2005 | Brun et al. |
| 2006/0104966 | A1 | 5/2006 | Green et al. |
| 2006/0275872 | A1 | 12/2006 | Kashiwagi et al. |
| 2010/0322903 | A1 | 12/2010 | Collins et al. |
| 2012/0021458 | A1 | 1/2012 | Suzuki et al. |
| 2012/0027694 | A1 | 2/2012 | Thijssen et al. |
| 2020/0237632 | A1 | 7/2020 | Szabados et al. |
| 2020/0370026 | A1 | 11/2020 | Yoshida |

FOREIGN PATENT DOCUMENTS

| | | | |
|---|---|---|---|
| EP | 0302529 | A2 | 2/1989 |
| WO | WO2019107288 | A1 | 6/2019 |

OTHER PUBLICATIONS

International Search Report and Written Opinion for International Application No. PCT/US2022/079573, dated Mar. 20, 2023, 17 pages.

Stiefel et al., "Reactions of cosmetic UV filters with skin proteins: model studies of ketones with primary amines," Trends in Photochemistry & Photobiology, 2013, 15:63-75.

International Search Report and Written Opinion for International Application No. PCT/US2021/032217, dated Sep. 30, 2021, 13 pages.

*Primary Examiner* — Robert A Wax
*Assistant Examiner* — Olga V. Tcherkasskaya
(74) *Attorney, Agent, or Firm* — Finnegan, Henderson, Farabow, Garrett & Dunner, LLP

(57) ABSTRACT

Sunscreen compositions and sunscreen active ingredients are disclosed herein which comprise at least one ketone-containing UV filter and at least one primary or secondary amine wherein at least one ketone-containing UV filter and at least one primary or secondary amine react to form an imine analog of the ketone-containing UV filter wherein the imine analog has at least one property selected from the group consisting of a) is capable of extending UV protection into a visible region equal to or greater than 400 nm, b) is water resistant, and/or c) prevents or decreases skin penetration. This imine analog may be further modified to provide a substrate capable of reacting with transglutaminase or any variant thereof and/or a lysyl oxidase to bind the sunscreen composition or sunscreen active ingredient to a target of interest. Also disclosed are cosmetic or pharmaceutical preparations comprising any of the sunscreen compositions or sunscreen ingredients along with a cosmetically or pharmaceutically acceptable carrier.

4 Claims, 8 Drawing Sheets

Specification includes a Sequence Listing.

Oxybenzone

Imine-1

Imine-2

Imine-3

Oxybenzone
Carbamate-1

Oxybenzone
N-Boc-Imine-6

Avobenzone

*N*-Boc-Imine-7

Imine-7

Sulisobenzone

*N*-Boc-Imine-8

Amodimethicone

Imine-10

Log P: 2.73
Oxybenzone

Log P: 4.92
Imine-1

Log P: 4.85
Imine-2

Log P: 3.12
Imine-3

Log P: 2.68
Imine-4

Log P: 1.79
Imine-5

Log P: 5.07
***N*-Boc-Imine-6**

Log P: 3.68
Imine-6

Log P: 7.52
Dimer-Imine-6

Log P: 4.3
Avobenzone

Log P: 6.65
***N*-Boc-Imine-7**

Log P: 5.25
Imine-7

Log P: 1.89
Sulisobenzone

Log P: 4.23
***N*-Boc-Imine-8**

Log P: 2.84
Imine-8

Log P: 5.71
DHHB

Log P: 8.06
***N*-Boc-Imine-9**

Log P: 6.67
Imine-9

SEQUENCE LISTING

<160> NUMBER OF SEQ ID NOS: 9

<210> SEQ ID NO 1
<211> LENGTH: 331
<212> TYPE: PRT
<213> ORGANISM: Streptomyces mobaraensis

<400> SEQUENCE: 1

```
Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
```

```
            100                 105                 110

Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330


<210> SEQ ID NO 2
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
        115                 120                 125
```

```
Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Glu Gly Ser Leu Gly Ala Met
        275                 280                 285

Ile Val Tyr Glu Ser Lys Phe Arg Asn Trp Lys Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330


<210> SEQ ID NO 3
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160
```

```
Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Lys Ala Pro Leu Gly Ala Met
        275                 280                 285

His Val Tyr Glu Ser Lys Phe Arg Asn Trp Val Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330


<210> SEQ ID NO 4
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
```

-continued

```
            180                 185                 190

Met Lys Ala Val Ile Tyr Ala Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ala Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330


<210> SEQ ID NO 5
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ala Lys His Phe Trp Ser Gly Gln Asp Arg
        195                 200                 205
```

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Val Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330

<210> SEQ ID NO 6
<211> LENGTH: 331
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Asp Pro Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Gly Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
245 250 255

Gly Trp Phe Gly Ala Gln Thr Glu Ala Asp Ala Asp Lys Thr Val Trp
260 265 270

Thr His Gly Asn His Tyr His Ala Pro Asn Gly Ser Leu Gly Ala Met
275 280 285

His Val Tyr Glu Ser Lys Phe Arg Asn Trp Val Glu Gly Tyr Ser Asp
290 295 300

Phe Asp Arg Gly Ala Tyr Val Ile Thr Phe Ile Pro Lys Ser Trp Asn
305 310 315 320

Thr Ala Pro Asp Lys Val Lys Gln Gly Trp Pro
325 330

<210> SEQ ID NO 7
<211> LENGTH: 331
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Asp Pro Asp Asp Arg Val Thr Pro Pro Ala Glu Pro Leu Asp Arg Met
1 5 10 15

Pro Asp Pro Tyr Arg Pro Ser Tyr Gly Arg Ala Glu Thr Val Val Asn
20 25 30

Asn Tyr Ile Arg Lys Trp Gln Gln Val Tyr Ser His Arg Asp Gly Arg
35 40 45

Lys Gln Gln Met Thr Glu Glu Gln Arg Glu Trp Leu Ser Tyr Gly Cys
50 55 60

Val Gly Val Thr Trp Val Asn Ser Gly Gln Tyr Pro Thr Asn Arg Leu
65 70 75 80

Ala Phe Ala Ser Phe Asp Glu Asp Arg Phe Lys Asn Glu Leu Lys Asn
85 90 95

Gly Arg Pro Arg Ser Gly Glu Thr Arg Ala Glu Phe Glu Gly Arg Val
100 105 110

Ala Lys Glu Ser Phe Asp Glu Glu Lys Gly Phe Gln Arg Ala Arg Glu
115 120 125

Val Ala Ser Val Met Asn Arg Ala Leu Glu Asn Ala His Asp Glu Ser
130 135 140

Ala Tyr Leu Asp Asn Leu Lys Lys Glu Leu Ala Asn Gly Asn Asp Ala
145 150 155 160

Leu Arg Asn Glu Asp Ala Arg Ser Pro Phe Tyr Ser Ala Leu Arg Asn
165 170 175

Thr Pro Ser Phe Lys Glu Arg Asn Gly Gly Asn His Asp Pro Ser Arg
180 185 190

Met Lys Ala Val Ile Tyr Ser Lys His Phe Trp Ser Gly Gln Asp Arg
195 200 205

Ser Ser Ser Ala Asp Lys Arg Lys Tyr Gly Asp Pro Asp Ala Phe Arg
210 215 220

Pro Ala Pro Gly Thr Gly Leu Val Asp Met Ser Arg Asp Arg Asn Ile
225 230 235 240

Pro Arg Ser Pro Thr Ser Pro Gly Glu Gly Phe Val Asn Phe Asp Tyr
245 250 255

Gly Trp Phe Gly Ala Gln Thr Glu Ala Asp Ala Asp Lys Thr Val Trp

-continued

```
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330


<210> SEQ ID NO 8
<211> LENGTH: 339
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285
```

-continued

```
His Val Tyr Glu Ser Lys Phe Arg Asn Trp Ser Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro Leu Glu His His His
                325                 330                 335

His His His


<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(8)
<223> OTHER INFORMATION: This sequence may encompass 6-8 residues

<400> SEQUENCE: 9

His His His His His His His His
1               5
```

SUNSCREEN COMPOSITIONS

CROSS-REFERENCE TO RELATED APPLICATIONS

This application is a continuation-in-part of PCT/US2021/032217 filed on May 13, 2021 which claims the benefit of U.S. Provisional Application No. 63/024,398, filed on May 13, 2020, and 63/074,288, filed on Sep. 3, 2020, all of which are incorporated by reference herein in their entireties.

STATEMENT REGARDING FEDERALLY SPONSORED RESEARCH

This invention was partially made with government support under Grant No. 2026057, awarded by the National Science Foundation. The government has certain rights in this invention.

INCORPORATION BY REFERENCE

The sequence listing provided in the file named 12527_011US1_jaj_SL.txt with a size of 24,366 bytes which was created on Nov. 23, 2021, and which is filed herewith, is incorporated by reference in its entirety.

FIELD

The field concerns sunscreen compositions comprising an imine analog of a ketone-containing UV filter that has at least one property selected from the group consisting of a) is capable of extending UV protection into a visible region equal to or greater than 400 nm, b) is water resistant, and/or c) prevents or decreases skin penetration.

BACKGROUND

Ultraviolet (UV) filters are compounds, mixtures, or materials that block or absorb UV light. One of the major applications of UV filters is their use as sunscreens to protect skin from sunburn and other sun/UV-related damage. Since excessive UV radiation can cause sunburn, photoaging and skin cancer, care products such as sunscreen usually include a classification for the specific wavelengths they filter. UV classifications include UVA (320-400 nm), UVB (290-320 nm) and UVC (200-280 nm). Broad spectrum sunscreens protect against both UVA and UVB rays.

UV-absorbing compounds are used not only in sunscreen, but also in other personal care products, such as lipstick, shampoo, hair spray, body wash, and insect repellant. Chemical filters protect against UV radiation by absorbing, reflecting or scattering it. Reflection and scattering are accomplished by inorganic UV filters, such as titanium dioxide and zinc oxide. Absorption, mainly of UVB, is done by organic UV filters.

The European Union determines broad spectrum protection by the ratio of UVA to UVB protection, requiring one third of the sun protection factor (SPF) number to be UVA protection. There are eight EU-approved UVA filters currently being used in European sunscreens. Some of the EU-approved UVA filters are triazine-containing UV filters. They also provide some UVB protection. Unfortunately, such compounds are still not FDA-approved for use in the United States, and it is not clear when such approval might be forthcoming.

Accordingly, there remains a need to develop new sunscreens using FDA-approved UV filters that might be comparable or even surpass the efficacy of these triazine-containing UV filters.

SUMMARY

In a first embodiment, there is disclosed a sunscreen composition comprising at least one ketone-containing UV filter and at least one primary or secondary amine wherein the ketone-containing UV filter and the at least one primary or secondary amine react to form an imine analog of the ketone-containing UV filter wherein said imine analog has at least one property selected from the group consisting of a) is capable of extending UV protection into a visible region equal to or greater than 400 nm, b) is water resistant, and/or c) prevents or decreases skin penetration.

In a second embodiment, the ketone-containing UV filter is selected from the group consisting of avobenzone, diethylamino hydroxybenzoyl hexyl benzoate, sulisobenzone, and oxybenzone.

In a third embodiment, the imine analog form of the ketone-containing UV filter may be further modified to provide a substrate capable of reacting with transglutaminase or any variant thereof and/or a lysyl oxidase to bind the sunscreen composition to a target of interest.

In a fourth embodiment, there is disclosed a sunscreen active ingredient comprising at least one ketone-containing UV filter and at least one primary or secondary amine wherein the ketone-containing UV filter and the at least one primary or secondary amine react to form an imine analog of the ketone-containing UV filter wherein said imine analog has at least one property selected from the group consisting of a) is capable of extending UV protection into a visible region equal to or greater than 400 nm, b) is water resistant, and/or c) prevents or decreases skin penetration. Preferably, the ketone-containing UV filter is selected from the group consisting of avobenzone, diethylamino hydroxybenzoyl hexyl benzoate, sulisobenzone, and oxybenzone.

In a fifth embodiment, the imine analog form of the ketone-containing UV filter of the sunscreen active ingredient is further modified to provide a substrate capable of reacting with transglutaminase or any variant thereof and/or a lysyl oxidase to bind said sunscreen active ingredient to a target of interest.

In a sixth embodiment, there is disclosed a cosmetic or pharmaceutical preparation comprising at least one of the sunscreen compositions or sunscreen active ingredient described herein and a cosmetically or pharmaceutically acceptable carrier.

BRIEF DESCRIPTION OF THE FIGURES AND SEQUENCES

Figure 1:
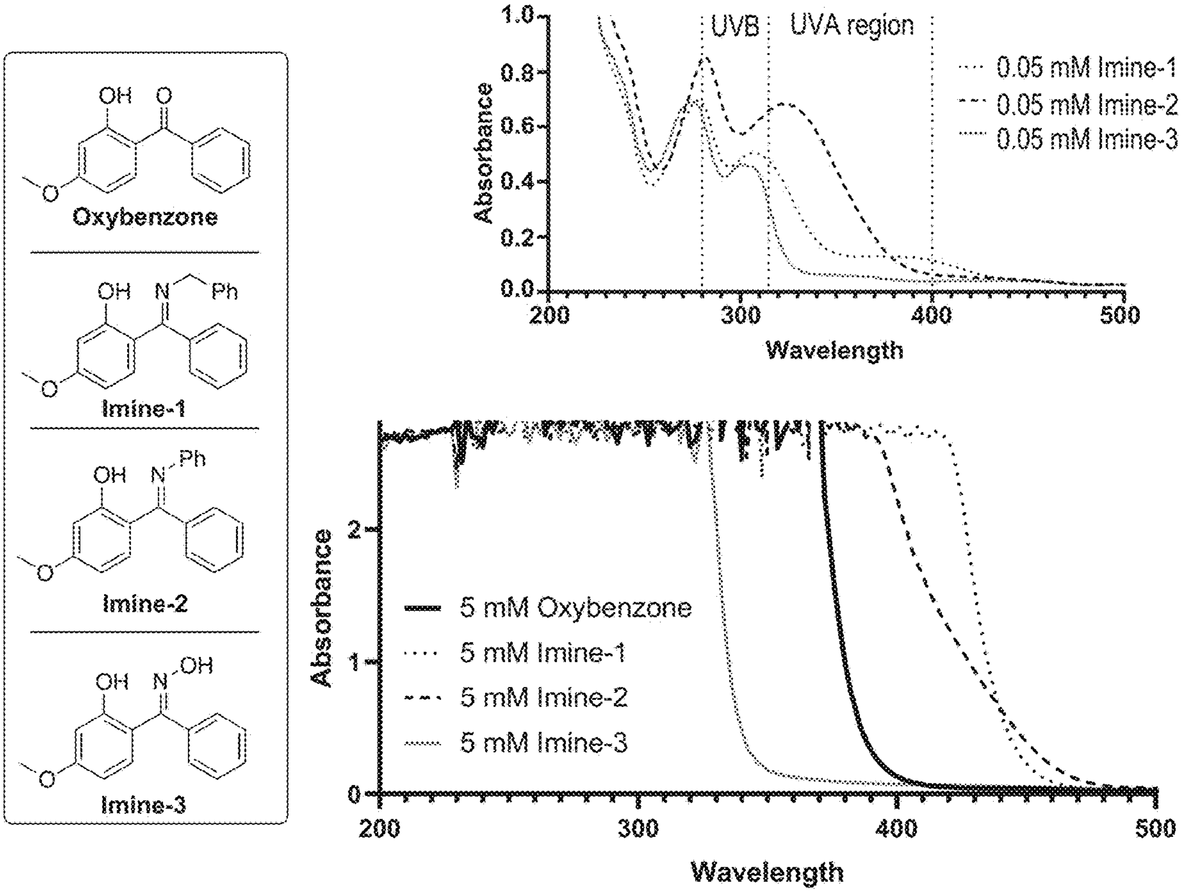
FIG. 1 depicts the UV/Vis spectral properties of Imine-1, Imine-2, and Imine-3 compared to oxybenzone in acetonitrile.

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NO:1 corresponds to the amino acid sequence of wild-type transglutaminase (Tgase) sequence of *Streptomyces mobaraensis*.

SEQ ID NO:2 corresponds to a variant of the sequence of SEQ ID NO:1 wherein this variant has a triple mutation (N282E, H289I, and S299K) relative to SEQ ID NO:1.

SEQ ID NO:3 corresponds to a variant of SEQ ID NO:1 wherein this variant has a quadruple mutation (N282K, G283A, S284P, and S299V) relative to SEQ ID NO:1.

SEQ ID NO:4 corresponds to a variant of SEQ ID NO:1 wherein this variant has a double mutation (S199A and S299A) relative to SEQ ID NO:1.

SEQ ID NO:5 corresponds to a variant of SEQ ID NO:1 wherein this variant has a double mutation (S199A and S299V) relative to SEQ ID NO:1.

SEQ ID NO:6 corresponds to a variant of SEQ ID NO:1 wherein this variant has a triple mutation (S2P, S199G and S299V) relative to SEQ ID NO:1.

SEQ ID NO:7 corresponds to a variant of SEQ ID NO:1 wherein this variant has a single mutation (S2P) relative to SEQ ID NO:1.

SEQ ID NO:8 corresponds to SEQ ID NO:1 with a polyhistidine tag, i.e., wild-type Tgase with a polyhistidine tag.

DETAILED DESCRIPTION

All patents, patent applications, and publications cited herein are incorporated by reference in their entireties.

Words using the singular include the plural, and vice versa, unless the context clearly dictates otherwise.

Throughout this application, various embodiments can be presented in a range format. It should be understood that the description in range format is merely for convenience and brevity and should not be construed as an inflexible limitation on the scope of the embodiments described herein. Accordingly, the description of a range should be considered to have specifically disclosed all the possible subranges as well as individual numerical values within that range. For example, description of a range, such as from 1 to 6 should be considered to have subranges such as from 1 to 2, from 1 to 3, from 1 to 4 and from 1 to 5, from 2 to 3, from 2 to 4, from 2 to 5, from 2 to 6, from 3 to 4, from 3 to 5, from 3 to 6, etc., as well as individual numbers within that range, for example, 1, 2, 3, 4, 5 and 6. This applies regardless of the breadth of the range.

In this disclosure, many terms and abbreviations are used. The following definitions apply unless specifically stated otherwise.

As used herein, the singular forms "a," "an," and "the" include plural references unless the context clearly dictates otherwise. For example, the term "a compound" or "at least one compound" may include a plurality of compounds, including mixtures thereof. The terms "a," "an," "the," "one or more," and "at least one," for example, can be used interchangeably herein.

The term "about" as used herein can allow for a degree of variability in a value or range, for example, within 10%, within 5%, or within 1% of a stated value or of a stated limit of a range.

The term "amino acid" refers to the basic chemical structural unit of a protein, peptide, or polypeptide. The following abbreviations used herein to identify specific amino acids can be found in Table 1.

TABLE 1

One and Three Letter Amino Acid Abbreviations

| Amino Acid | Three-Letter Abbreviation | One-Letter Abbreviation |
|---|---|---|
| Alanine | Ala | A |
| Arginine | Arg | R |
| Asparagine | Asn | N |
| Thermostable serine acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

The terms "and/or" and "or" are used interchangeably herein and refer to a specific disclosure of each of the two specified features or components with or without the other. Thus, the term "and/or" as used in a phrase such "A and/or B" herein is intended to include "A and B," "A or B," "A" (alone), and "B" (alone). Likewise, the term "and/or" as used a phrase such as "A, B and/or C" is intended to encompass each of the following aspects: A, B and C; A, B or C; A or C A or B; B or C; A and C; A and B; B and C; A (alone); B (alone); and C (alone).

The term "avobenzone" refers to a chemical compound $C_{20}H_{22}O_3$ (CAS Registry Number 70356-09-1) that absorbs UVA radiation and is used as an ingredient in sunscreens. UVA radiation is the type of UV light that contributes to skin cancer and aging of the skin. However, avobenzone degrades in sunlight so it usually is combined with other ingredients to be effective. It is approved by the FDA in concentrations up to 3%. Avobenzone is marketed under the trademark Parsol®.

The term "composition" refers to a combination of two or more substance or compounds.

The terms "comprises," "comprising," "includes," "including," "having" and their conjugates are used interchangeably and mean "including but not limited to." It is understood that wherever aspects are described herein with the language "comprising," otherwise analogous aspects described in terms of "consisting of" and/or "consisting essentially of" are also provided.

The term "consisting of" means "including and limited to."

The term "consisting essentially of" means the specified material of a composition, or the specified steps of a methods, and those additional materials or steps that do not materially affect the basic characteristics of the material or method.

As used herein with regard to amino acid residue positions, "corresponding to" or "corresponds to" or "correspond to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related protein or a reference protein.

One of ordinary skill in the art will appreciate that modifications of amino acid sequences disclosed herein can be made while retaining the function associated with the disclosed amino acid sequences. For example, it is well known in the art that alterations in a gene which result in the production of a chemically equivalent amino acid at a given site, but do not affect the functional properties of the encoded protein, are common.

The term "cosmetic" refers to most personal care, skin care, make-up and cosmetics. A cosmetic is any substance or preparation intended to be placed in contact with any part of the human body, with a view to altering body odors, changing its appearance, cleansing it, maintaining it in good condition, perfuming it, and/or protecting it. Cosmetics include, but are not limited to soap, shampoo and conditioner, moisturizer, bath bombs, hair dye, perfume, lipstick, mascara, nail polish, deodorant and many other products. A "cosmetic preparation" is in ready-to use-form.

The term "DHHB" refers to diethylamino hydroxybenzoyl hexyl benzoate having molecular formula C24H31NO4 (CAS Registry Number 302776-68-7). DHHB is a UV filter with high absorption in the UV-A range. It was approved in Europe in 2005.

The term "derived from" encompasses the terms "originated from," "obtained from," "obtainable from," "isolated from," "purified from," and "created from," and generally indicates that one specified material finds its origin in another specified material or has features that can be described with reference to another specified material.

The term "imine" refers to any of a class of organic nitrogen compounds having the general formula $R_2C{=}NR$; they are tautomeric with "enamines." Tautomers are structural isomers of chemical compounds that readily interconvert. Thus, the term "imine" as used herein refers to both the "imine" and its corresponding structural isomer, the "enamine." The terms "structural isomer" and "tautomer" are used interchangeably herein.

The terms "isolated," "purified," "separated," and "recovered" as used herein refer to a material (e.g., a protein, nucleic acid, or cell) that is removed from at least one component with which it is naturally associated. For example, these terms may refer to a material which is substantially or essentially free from components which normally accompany it as found in its native state, such as, for example, an intact biological system. An isolated nucleic acid molecule includes a nucleic acid molecule contained in cells that ordinarily express the nucleic acid molecule, but the nucleic acid molecule is present extrachromosomally or at a chromosomal location that is different from its natural chromosomal location.

The term "ketone-containing UV filter" refers to any compounds or mixtures of compounds a) containing a carbonyl moiety in which a carbon atom is covalently bonded to an oxygen atom as depicted by the structure: $R_2C{=}O$, wherein R can be a variety carbon-containing substituents, i.e., R is not a hydrogen atom; and b) such compounds or mixtures of compounds are also capable of blocking or absorbing UV light.

The term "lysyl oxidase" ("LOX") (also known as protein-lysine 6-oxidase) refers to copper-dependent enzymes that catalyze formation of aldehydes from lysine residues in collagen and elastin precursors. These aldehydes are highly reactive and undergo spontaneous chemical reactions with other lysyl oxidase-derived aldehyde residues, or with unmodified lysine residues. This results in cross-linking collagen and elastin. LOX proteins have been identified in animals, other eukaryotes, and in bacteria and archaea (reviewed in Grau-Bove, et al. (2015) *Scientific Reports* 5: Article number: 10568).

The term "mutation" herein refers to a change introduced into a parental sequence, including, but not limited to, substitutions, insertions, and deletions (including truncations), thereby producing a "mutant." The consequences of a mutation include, but are not limited to, the creation of a new character, property, function, phenotype or trait not found in the protein encoded by the parental sequence.

"Optional" or "optionally" means that the subsequently described event, circumstance, or material may or may not occur or be present, and that the description includes instances where the event, circumstance, or material occurs or is present and instances where it does not occur or is not present.

The term "oxybenzone" refers to a chemical organic compound having molecular formula $C_{14}H_{12}O_3$(CAS Registry Number 131-57-7). It is a benzophenone derivative used as a sunscreen agent. It is approved by the FDA in concentrations up to 6%. It absorbs UVB radiation and some UVA radiation.

The terms "peptides," "proteins," and "polypeptides" are used interchangeably herein and refer to a polymer of amino acids joined together by peptide bonds. A "protein" or "polypeptide" comprises a polymeric sequence of amino acid residues. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S". When describing modifications, a position followed by amino acids listed in parentheses indicates a list of substitutions at that position by any of the listed amino acids. For example, 6(L, I) means position 6 can be substituted with a leucine or isoleucine. At times, in a sequence, a slash (/) is used to define substitutions, e.g., F/V, indicates that the position may have a phenylalanine or valine at that position.

The term "pharmaceutical preparation" refers to a drug intended for human or veterinary use, presented in its finished dosage form, i.e., ready to use.

The term "primary amine" refers to organic derivatives of ammonia in which one of the hydrogen atoms has been replaced, for example, including but not limited to, by an unsubstituted or substituted alkyl, a cyclic alkyl or an aromatic/heteroaromatic group.

The term "secondary amine" refers organic derivatives of ammonia in which two of the hydrogen atoms are replaced, for example, including but not limited to, by unsubstituted or substituted alkyl and/or aromatic/heteroaromatic groups.

The term "sulisobenzone" refers to 5-benzoyl-4-hydroxy-2-methoxybenzenesulfonic acid having molecular formula $C_{14}H_{12}O_6S$ (CAS Registry Number 4065-45-6). It is approved by the FDA in concentrations up to 10%. It works to filter out UVA and UVB rays. It is used as a UV-filter ingredient in sunscreens and other personal care products.

The terms "sunscreen" and "sunscreen composition" are used interchangeably herein and refer to any compound, substance, mixtures, or material that is capable of blocking or absorbing UV radiation. It can be regarded as a photo-protective topical agent.

The term "sunscreen active ingredient" refers to that part of a compound or substance that produces the desired chemical or biological effect which in this case involves the blocking, reflection or absorption of UVA and UVB radiation.

The term "target of interest" refers to any exogenous protein or peptide such as a dermatologically relevant protein, or any part of a human body or animal body, suitable for binding to an imine form of any ketone-containing UV filter that has been modified to serve as a substrate for a Tgase or any variant thereof. The Tgase or any variant thereof then catalyzes a reaction whereby the modified imine is conjugated/linked to the relevant part of the human body, i.e., the target of interest. For example, the target of interest may include, but is not limited to, glutamine-glycine, collagen, keratin and/or elastin.

The term "transglutaminase" (Tgase EC 2.3.2.13) refers to enzymes capable of catalyzing an acyl transfer reaction in which a γ-carboxy-amide group of a peptide-bound glutamine residue is the acyl donor. Primary amino groups in a variety of compounds may function as acyl acceptors with the subsequent formation of monosubstituted γ-amides of peptide bound glutamine. When the ε-amino group of a lysine residue in a peptide chain serves as the acyl acceptor, the Tgases form intramolecular or intermolecular γ-glutamyl-ε-lysyl crosslinks. The catalytic reaction proceeds via glutamine deamination and formation of a protein-glutamyl-thioester at the active site of the enzyme. Nucleophilic attack by a lysyl ε-amino group of a second protein at the carbonyl moiety of the thioester intermediate generates isopeptide-crosslinked proteins that are largely resistant to proteolysis by common peptidases (Mariniello, et al. (2007) *J Agr Food Chem.* 55:4717-4721).

Bonds formed by a Tgase exhibit high resistance to proteolytic degradation (proteolysis). Tgases from microbial origin are calcium-independent, which represents a major advantage for their practical use. Tgase has found many applications in biotechnology and in the food processing industry, where it has earned the moniker "meat glue." The peptide crosslinking activity has been shown to be useful for a variety of industrial purposes ranging from food processing, biotechnology, pharmaceuticals, medical devices, personal and household goods, and leather and textile treatment. The most commonly used Tgase is microbial transglutaminase from *Streptomyces mobaraensis*, having the amino acid sequence depicted in SEQ ID NO:1 and referred to hereinafter as Tgase.

The term "UV filter" refers to any compounds, mixture, substances, or materials that block, reflect, or absorb UV light.

The term "UV light" refers to a form of electromagnetic radiation with a wavelength from 10 nm to 400 nm which falls in range of the electromagnetic spectrum between visible light and X-rays. There are three types or bands UV light—UVA, UVB, and UVC. UVA has a wavelength in the range of 320-400 nm. It is not absorbed by the ozone layer. UVA rays are further classified into UVA1 and UVA 2. UVA1 is between 340 and 400 nm whereas UVA2 is between 320 and 340 nm in wavelength. UVB has a wavelength in the range 290-320 nm. It is mostly absorbed by the ozone layer, but some does reach the surface of earth. UVC has a wavelength in the range 100-290 nm. It is completely absorbed by the ozone layer and the earth's atmosphere.

Related (and derivative) proteins encompass "variant" or "mutant" proteins, which terms are used interchangeably herein. Variant proteins differ from another (i.e., parental) protein and/or from one another by a small number of amino acid residues. A variant may include one or more amino acid mutations (e.g., amino acid deletion, insertion or substitution) as compared to the parental protein from which it is derived. Alternatively or additionally, variants may have a specified degree of sequence identity with a reference protein or nucleic acid, e.g., as determined using a sequence alignment tool, such as BLAST, ALIGN, and CLUSTAL. For example, variant proteins or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence and integer percentage therebetween.

The term "visible light" refers to a form of electromagnetic radiation that is perceived by the human eye with a wavelength from 400 nm to 700 nm which falls in the range of the electromagnetic spectrum between UV light and infrared light. Within visible light, high energy visible light (HEVL) with a wavelength from 400 nm to 450 nm is particularly important for causing oxidative stress, free radical generation and dermal cellular damage to the skin.

The term "visible light filter" refers to any compounds, mixture, substances, or materials that block, reflect, or absorb UV light.

The term "wild-type" in reference to an amino acid sequence or nucleic acid sequence indicates that the amino acid sequence or nucleic acid sequence is a native or naturally occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant/engineered nucleic acids and protein sequences produced in the laboratory or modification of the wild-type sequence).

As is discussed above, ultraviolet filters also referred to as sunscreens or sun protectants, are the elements present in photo-protector formulas that interfere directly with the incident solar radiation through absorption, reflection or dispersion of energy. They are classified into two categories based on their mechanism of action: chemical or organic sunscreens and mineral-based or organic sunscreens.

In the United States, sunscreen products are classified as over-the-counter (OTC) drugs. This means that they are strictly regulated and require pre-market registration with the U.S. Food and Drug Administration (FDA). Regulation on sunscreens includes Sunscreen Drug Products for Over-The-Counter Human Use Monograph (21 CFR 352) and the Sunscreen Innovation Act. The U.S. FDA in February 2019 issued a proposed rule that would alter the regulations associated with the manufacturing and selling of sunscreen, as well as other sun-care related products. This proposed rule is aimed at bringing nonprescription, OTC sunscreens that are marketed without FDA-approved application, together with the latest science to better ensure that consumers have access to safe and effective preventative sun care options.

Of the 16 currently marketed sunscreen active ingredients, two ingredients, zinc oxide and titanium oxide, are GRASE (Generally Recognized as Safe and Effective) for use in sunscreens. Two ingredients, para-aminobenzoic acid (PABA) and trolamine salicylate, were considered not GRASE for use in sunscreens. The remaining twelve ingredients, cinoxate, dioxybenzone, ensulizole, homosalate, meradimate, octinoxate, octisalate, octocrylene, padimate O, sulisobenzone, oxybenzone and avobenzone, were deemed to have insufficient safety data to make a positive GRASE determination.

In contrast, the European Union regards sunscreens as cosmetics. Since this classification is so different from the U.S. classification, a number of ingredients used in European sunscreens, such as triazine-containing UV filters, currently are not allowed on the U.S. market without oversight. It remains to be seen what will happen regarding sunscreen development in the U.S. Thus, a need for new sunscreen active ingredients continues to exist.

Disclosed herein is a sunscreen composition comprising at least one ketone-containing UV filter and at least one primary or secondary amine wherein the ketone-containing UV filter react to form an imine analog of the ketone-containing UV filter wherein said imine analog.

has at least one property selected from the group consisting of a) is capable of extending UV protection into a visible region equal to or greater than 400 nm, b) is water resistant, and/or c) prevents or decreases skin penetration.

Thus, the sunscreen compositions disclosed herein comprising at least one ketone-containing UV filter and at least one primary or secondary amine wherein the ketone-containing UV filter react to form an imine analog of the ketone-containing UV filter wherein said imine analog has at least one property selected from the group consisting of a) is used as a UV filter and visible light filter, b) is water resistant, and/or c) prevents or decreases skin penetration.

This is accomplished without the need of adding another component to provide a visible light filter function (such as iron oxide pigments), drawbacks associated with visible light filters may be avoided, and fewer active ingredients are in contact with the skin, potentially minimizing the risk of allergic reaction and/or irritation of the skin. Furthermore, the sunscreen compositions described herein can be manufactured more easily than a multicomponent system, suitably at a lower cost. Furthermore, in contrast to use the use of two ingredients as a UV filter and visible light filter respectively, each having its own absorbance profile, the sunscreen compositions disclosed herein provide continuous photoprotection extended from UV light to visible light range. And so possible wavelength coverage gaps and/or variations in the extent of protection arising from the (potentially incomplete) overlap of absorbance profiles between the UV filter ingredient and the visible light filter ingredient are avoided. In the embodiments of the sunscreen composition described herein, such sunscreen compositions are free of, or substantially free of, other visible light filters. For example, free of, or substantially free of, pigments such as iron oxide.

The visible light filter of the sunscreen compositions described herein preferably block or absorb visible light of a wavelength from 400 nm to 450 nm.

Examples of ketone-containing UV filters include, but are not limited to, avobenzone, oxybenzone, sulisobenzone, enzacamene, diethylamino hydroxybenzoyl hexyl benzoate and ecamsule. Preferred ketone-containing UV filters are avobenzone, diethylamino hydroxybenzoyl hexyl benzoate (DHHB), sulisobenzone, and oxybenzone. It is expected that most amines capable of reacting with a ketone-containing UV filter to produce the desired imine analog will be useful provided that the imine analog also has at least one property selected from the group consisting of a) is capable of extending absorbance into the UVA-1, UVA-2, and/or UVB regions as well as into the visible region equal to or greater than 400 nm, b) is water resistant, and/or c) prevents or decreases skin penetration. Examples of such useful amines include, but are not limited to, amino acids, cadaverine, putrescine, hydrazine, adipic acid dihydrazide, sebacic dihydrazide, ethylenediamine, hexamethylenediamine, benzyl amine, aniline, amodimethicone, tromethamine, polyethylenimine, polylysine, dimethylaminopropylamine, aminomethyl propanol, etc.

Figure 8:
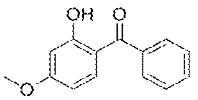
FIG. 8 depicts the structures of avobenzone, oxybenzone, sulisobenzone, DHHB, and the imines described in the Examples below along with their estimated Log P values as determined by ChemDraw.
Figure 8:
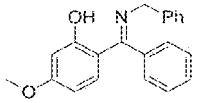
Figure 8:
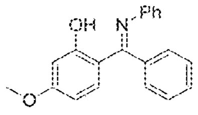
Figure 8:
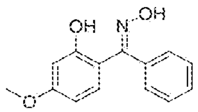
Figure 8:
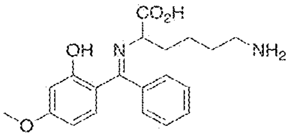
Figure 8:
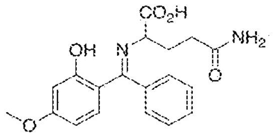
Figure 8:
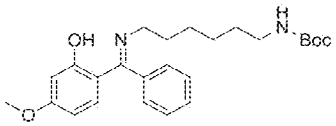
Figure 8:
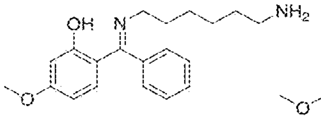
Figure 8:
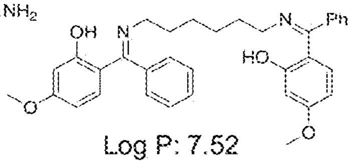
Figure 8:
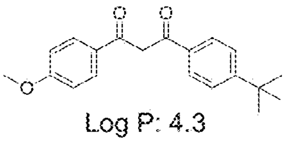
Figure 8:
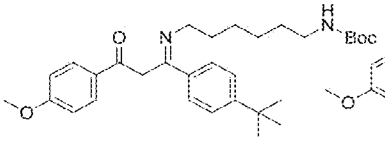
Figure 8:
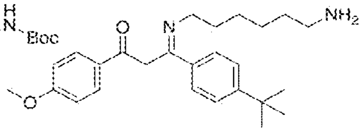
Figure 8:
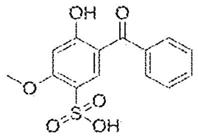
Figure 8:
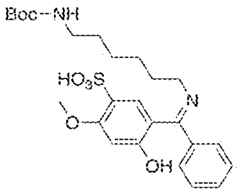
Figure 8:
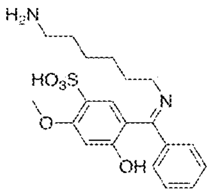
Figure 8:
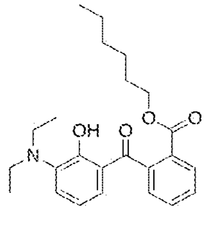
Figure 8:
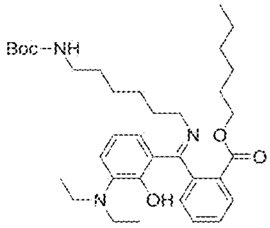
Figure 8:
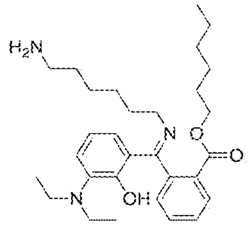

When the at least one ketone-containing UV filter and the at least one primary or secondary amine are added to a reactor, they are capable of reacting to form an imine analog of the ketone-containing UV filter. Preferably, the imine analog is selected from one or more of imine-1, imine-2, imine-4, imine-5, imine-6, imine-7, imine-8, imine-9, N-Boc-Imine 7, N-Boc-Imine 8, N-Boc-Imine 9, and/or imine-10 as shown in FIG. 8 along with their estimate Log P values as calculated by ChemDraw. In some cases, the resulting imine analog may dimerize, for example, Dimer-Imine 6 as shown in FIG. 8. In another aspect, the resulting imine analog may be regarded as a reaction product of a ketone-containing UV filter and a primary or secondary amine. The imine analog of the present embodiments functions simultaneously as a UV filter and a visible light filter and/or is water resistant and/or decreases skin penetration.

Surprisingly and unexpectedly, it has been found that formation of this imine analog of the ketone-containing UV filter has at least one property selected from the group consisting of a) is capable of extending absorbance into the UVA-1, UVA-2, and/or UVB regions as well as into the visible region equal to or greater than 400 nm, b) is water resistant, and/or c) prevents or decreases skin penetration. It is believed that this is the first imine-containing sunscreen composition or sunscreen ingredient to have at least one of these properties as discussed herein. This is shown in greater detail below in the Examples and in the Figures provided herein.

In a further embodiment, there is a use of the sunscreen compositions disclosed herein comprising an imine analog of a ketone-containing UV filter as a visible light filter, wherein said imine analog is a reaction product of a ketone-containing UV filter and a primary or secondary amine.

Chemical UV-filters are required to remain on the surface, for example, of skin, to maintain their photoprotective character. Skin penetration of UV-filters in sunscreen products should be avoided. In addition to reduction of UV-protection due to skin penetration, photosensitivity reactions may also occur.

The success of topical delivery depends on the ability to overcome biological barriers such as the skin. When it comes to sunscreen safety, the goal is to limit skin penetration of chemicals from the topical formulations to avoid toxicity. The 500 Dalton rule postulates that the molecular weight (MW) of a compound should be under 500 Dalton to allow skin absorption. (Bos et al., Exp Dermatol 2000: 9:165-169). Thus, based on this rule, the UV-filter in a sunscreen composition should have a MW of at least 500 Dalton to reduce the likelihood of skin penetration.

Another useful value, in addition to MW, in assessing whether a substance will be absorbed by plants, animals, humans or other living tissue; or be easily carried away and disseminated by water, is the Log P value. It is an important molecular physical property that impacts a wide range of systems. The partition coefficient (P) is the ratio of concentrations of a compound in a mixture of two immiscible solvents at equilibrium. This ratio is therefore a comparison of the solubilities of the solute in these two liquids, specifically for un-ionized solutes. When one of the solvents is water and other is a non-polar solvent, then the Log P value is a measure of lipophilicity or hydrophobicity. Lipophilicity is a key determinant of permeability across tissue membranes. A negative value for log P means the compound has a higher affinity for the aqueous phase, i.e., it is more hydrophilic. A positive value for Log P denotes a higher concentration in the lipid phase, i.e., the compound is more lipophilic.

Generally, it is believed that small and moderately lipophilic molecules having a MW less than 500 Dalton and a Log P of 1-3 would be expected to penetrate the skin very well. Given this, it appears that moderately lipophilic molecules having a Log P in the range of 4-6 would be suitable for use as a UV-filter in sunscreens.

The terms "water-resistant" or "very water-resistant" have replaced the term "waterproof" with respect to sunscreen compositions. The terms "water-resistant" or "very water-resistant" can be used when the sun protection provided by a sunscreen product is reduced by less than 50% after a lukewarm bath lasting 40 minutes or 80 minutes, respectively. When sunscreen "sticks" to the skin, it is less likely to wash off in the water or when performing intense, sweat-inducing exercise.

As was noted above oxybenzone is a ketone-containing filter that can be contacted with a primary or secondary amine to form an imine analog thereof. It is also possible to combine 2 equivalents of oxybenzone or a similar ketone-containing compound with one equivalent of a diamine, such as hexamethylene diamine, to dimerize the oxybenzone via an imine. This is depicted in FIG. 8. The resulting dimer would have a MW above 500 Daltons and a Log P above the 1-3 range while retaining all the benefits afforded by expanding the range of UV protection into the visible range equal to or greater than 400 nm.

In addition to the UV filters described herein, the sunscreen compositions of the embodiments suitably comprise water, emulsifier, humectant, emollient, thickener, preservative, chelating agent, and/or other conventional ingredients in appropriate amounts. Preferably the sunscreen composition comprises 1.0-20% w/w % of the UV filters described herein.

In another aspect, the imine analogs of the ketone-containing UV filters disclosed herein may be further modified to provide a substrate capable of reacting with transglutaminase or any variant thereof and/or a lysyl oxidase to bind the sunscreen composition or sunscreen active ingredient to a target of interest.

There are Tgase enzymes that are variants of the $Ca^{2+}$-independent microbial transglutaminase (Tgase) *Streptomyces mobaraensis*. The wild-type enzyme from *Streptomyces mobaraensis* corresponds to the amino acid sequence set forth in SEQ ID NO:1.

Tgase variants of SEQ ID NO:1 may be obtained by mutating at one or more amino acids in the polypeptide sequence of the wild type Tgase and observing transglutaminase transamidation activity between a glutamine amino acid residue and an amine (or hydroxylamine) acceptor. Methods for recombinant expression of proteins with mutational substitutions have been described previously and are well known in the art, for example, *Molecular Cloning, A Laboratory Manual* 4th ed., Cold Spring Harbor Press (1989), Current *Protocols in Molecular Biology*, John Wiley & Sons (1987-1997) and the like. Combinations of point mutations can be generated using a number of methods including error-prone PCR, gene shuffling, molecular breeding, and the like.

Tgase variants and wild-type Tgase may further comprise a polyhistidine peptide extension at their C-terminus, as exemplified with amino acid residues 334-339 of SEQ ID NO:8. The polyhistidine peptide is a useful tag for purification purposes and does not affect enzymatic activity. Typically, the polyhistidine peptide is 6-8 residues long (SEQ ID NO: 9).

Tgase variants may further comprise a methionine residue at their N-terminus. The mature wild-type *Streptomyces mobaraensis* Tgase enzyme lacks the N-terminal methionine residue encoded by the gene sequence that encodes the enzyme. In some embodiments, the Tgase variant is expressed as a variant of the mature *Streptomyces mobaraensis* Tgase without an N-terminal methionine residue. In other embodiments, the Tgase is expressed as the mature Tgase with an additional N-terminal methionine residue, which may be provided by an expression vector from which the Tgase is expressed. Tgase variants of interest can be found in the amino acid sequences of SEQ ID NOs: 2, 3, 4, 5, 6, or 7.

As was noted above, the "target of interest" refers to any exogenous protein or peptide such as a dermatologically relevant protein, or any part of a human body or animal body, suitable for binding to an imine or enamine form of any ketone-containing UV filter that has been modified to serve as a substrate for a Tgase or any variant thereof. The Tgase or any variant thereof then catalyzes a reaction whereby the modified imine or enamine is conjugated/linked to the relevant part of the human body, i.e., the target of interest. For example, the target of interest may include, but is not limited to, glutamine-glycine, collagen, keratin and/or elastin.

Also encompassed within the scope of this disclosure are cosmetic or pharmaceutical preparations comprising any of the sunscreen compositions or sunscreen active ingredients disclosed herein along with a cosmetically or pharmaceutically acceptable carrier. For example, any of the imine analogs of the ketone-containing UV filters disclosed herein may or may not be further modified to provide a substrate capable of reacting with transglutaminase or any variant thereof and/or a lysyl oxidase to bind the sunscreen composition or sunscreen active ingredient to a target of interest.

Suitable cosmetically and pharmaceutically acceptable carries are well known in the art. Examples of cosmetically acceptable carriers include, but are not limited to, water and/or water-soluble solvents, aqueous gels, alcoholic gels, ointments, oils, alcoholic or aqueous fluids, water in oil emulsions, water in silicone emulsions, etc. Non-limiting examples of cosmetically acceptable carrier include glycerin, C1-4 alcohols, organic solvents, fatty alcohols, fatty ethers, fatty esters, polyols, glycols, vegetable oils, mineral oils, liposomes, laminar lipid materials.

Examples of organic solvents include, but are not limited to, monoalcohols and polyols such as ethyl alcohol, isopropyl alcohol, propyl alcohol, benzyl alcohol, and phenylethyl alcohol, or glycols or glycol ethers, such as, monomethyl, monoethyl and monobutyl ethers or ethylene glycol, propylene glycol, butylene glycol, hexylene glycol, dipropylene glycol as well as alkyl ethers of diethylene glycol for example monoethyl ether or monobutyl ether of diethylene glycol. Other suitable examples of organic solvents are ethylene glycol, propylene glycol, butylene glycol, hexylene, glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example dipropylene glycol n-butyl ether, isodecane, mineral oil, propylene glycol, pentylene glycol, hexylene glycol, glycerol and mixtures thereof.

A pharmaceutical or drug carrier is any substrate used in the process of drug delivery which serves to improve the selectivity, effectiveness, and/or safety of drug administration. Drug carriers can be used to control the release of a drug into systemic circulation.

Examples of pharmaceutically acceptable carriers include, but are not limited to, creams, emulsions, gels, liposomes, nanoparticles, microspheres, polymeric micelles, nanofibers, protein-drug complexes and/or ointments.

Non-limiting embodiments of the foregoing disclosed herein:

1. A sunscreen composition comprising at least one ketone-containing UV filter and at least one primary or secondary amine wherein the ketone-containing UV filter and the at least one primary or secondary amine react to form an imine analog of the ketone-containing UV filter wherein said imine analog has at least one property selected from the group consisting of a) is capable of extending UV protection into a visible region equal to or greater than 400 nm, b) is water resistant, and/or c) prevents or decreases skin penetration.

2. The sunscreen composition of embodiment 1 wherein the ketone-containing UV filter is selected from the group consisting of avobenzone, diethylamino hydroxybenzoyl hexyl benzoate (DHHB), sulisobenzone, and oxybenzone.

3. The sunscreen composition of embodiment 2 wherein the imine analog form of the ketone-containing UV filter is further modified to provide a substrate capable of reacting with transglutaminase or any variant thereof and/or a lysyl oxidase to bind said sunscreen composition to a target of interest.

4. A sunscreen active ingredient comprising at least one ketone-containing UV filter and at least one primary or secondary amine wherein the ketone-containing UV filter and the primary or secondary amine react to form an imine analog has at least one property selected from the group consisting of a) is capable of extending UV protection into a visible region equal to or greater than 400 nm, b) is water resistant, and/or c) prevents or decreases skin penetration.

5. The sunscreen active ingredient of embodiment 4 wherein the ketone-containing UV filter is selected from the group consisting of avobenzone, diethylamino hydroxybenzoyl hexyl benzoate, sulisobenzone, and oxybenzone.

6. The sunscreen active ingredient of embodiment 4 or 5 wherein the imine analog form of the ketone-containing UV filter is further modified to provide a substrate capable of reacting with transglutaminase or any variant thereof and/or a lysyl oxidase to bind said sunscreen active ingredient to a target of interest.

7. A cosmetic or pharmaceutical preparation comprising the sunscreen composition of embodiment 1 or 2 or the sunscreen active ingredient of embodiment 4 or 5 and a cosmetically or pharmaceutically acceptable carrier.

8. A cosmetic or pharmaceutical preparation comprising the sunscreen composition of embodiment 3 or the sunscreen active ingredient of embodiment 6 and a cosmetically or pharmaceutically acceptable carrier.

EXAMPLES

Unless defined otherwise herein, all technical and scientific terms used herein have the same meaning as commonly understood by one of ordinary skill in the art to which this disclosure belongs. Singleton, et al., *DICTIONARY OF MICROBIOLOGY AND MOLECULAR BIOLOGY,* 2D ED., John Wiley and Sons, New York (1994), and Hale & Marham, *THE HARPER COLLINS DICTIONARY OF BIOLOGY*, Harper Perennial, N.Y. (1991) provide one of skill with a general dictionary of many of the terms used with this disclosure.

The disclosure is further defined in the following Examples. It should be understood that these Examples, while indicating certain embodiments, are given by way of illustration only.

From the above discussion and the Examples, one skilled in the art can ascertain essential characteristics of this disclosure, and without departing from the spirit and scope thereof, can make various changes and modifications to adapt to various uses and conditions

Example 1. Synthesis and Analysis of Oxybenzone Series of Imines, Exploring Aromaticity a. Synthesis of Imine-1.

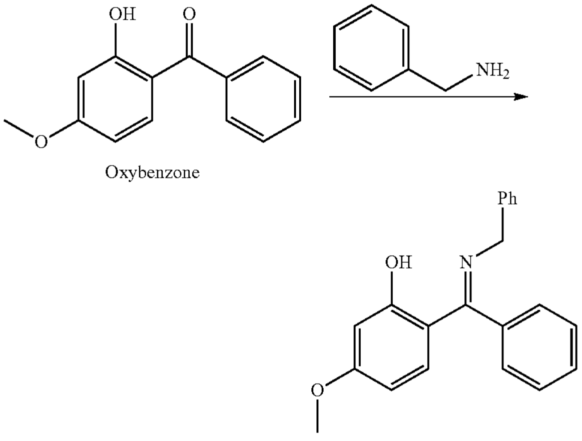

Oxybenzone

Imine-1

To a solution of oxybenzone (301 mg, 1.32 mmol, 1 eq) and benzylamine (169 mg, 1.58 mmol, 1.2 eq) in toluene (3 mL) was added tetraisopropoxytitanium (747 mg, 2.63 mmol, 2 eq) at 25° C. The reaction mixture was heated to 80° C. for 12 hr and monitored by LCMS. The reaction was quenched by dilution in water (20 mL) and the product was extracted with EtOAc (30 mL×3). The combined organic layers were washed with brine (30 mL), dried over $Mg_2SO_4$ and concentrated. The crude product was triturated with 1-[2-(4-methylphenoxy)ethyl]-2-[(2-phenoxyethyl)sulfanyl]-1H-benzimidazole (METB) (3 mL) at 25° C. for 15 min and filtered. The filter cake was dried under vacuum to give Imine-1 (171 mg, 41% yield,) as green solid, confirmed by LCMS and $^1$H NMR ($CDCl_3$).

b. Synthesis of Imine-2.

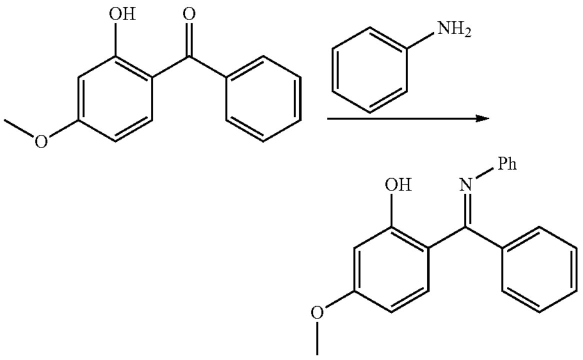

Imine-2

To a solution of oxybenzone (300 mg, 1.31 mmol, 1 eq) and aniline (147 mg, 1.58 mmol, 1.2 eq) in toluene (3 mL) was added tetraisopropoxytitanium (747 mg, 2.63 mmol, 2 eq) at 25° C. The reaction mixture was heated to 80° C. for 12 hr and monitored by LCMS. The reaction was quenched by dilution in water (20 mL) and the product was extracted with EtOAc (30 mL×3). The combined organic layers were washed with brine (30 mL), dried over $Mg_2SO_4$ and concentrated. The crude product was triturated with METB (3 mL) at 25° C. for 15 min and filtered. The filter cake was dried under vacuum to give Imine-2 (75 mg, 18% yield) as green solid, confirmed by LCMS and $^1$H NMR ($CDCl_3$).

c. Synthesis of Imine-3.

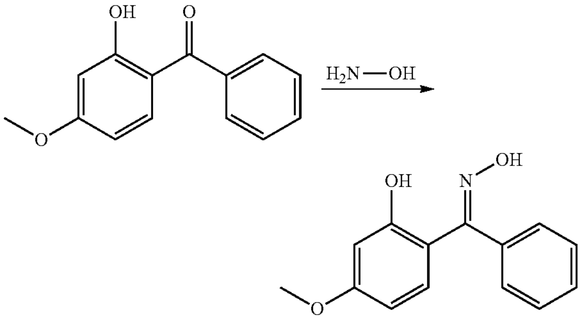

Imine-3

To a solution of oxybenzone (300 mg, 1.31 mmol, 1 eq) and hydroxylamine hydrochloride (109 mg, 1.58 mmol, 1.2 eq) in toluene (3 mL) was added tetraisopropoxytitanium (747 mg, 2.63 mmol, 2 eq) at 25° C. The reaction mixture was heated to 80° C. for 12 hr and monitored by LCMS. The reaction was quenched by dilution in water (20 mL) and the product was extracted with EtOAc (30 mL×3). The combined organic layers washed with brine (30 mL), dried over $Mg_2SO_4$ and concentrated. The crude product was purified by reversed-phase HPLC (column: Xtimate C18 150*40 mm*10 um; mobile phase: [water (NH3H2O+NH4HCO3)-ACN]; B %: 35%-75%, 10 min) to give Imine-3 (82 mg, 25% yield) as off-white solid, confirmed by LCMS and $^1$H NMR ($CDCl_3$).

d. UVA and UVB Absorption Properties.

Imine-1, Imine-2, and Imine-3 were synthesized, purified, and isolated (see above). All three compounds were separately dissolved in acetonitrile to a final concentration of 5 mM (FIG. 1) or 0.05 mM (FIG. 1, inset) and analyzed by UV/Vis (Cary-50 Spectrophotomer). The spectral properties were compared to oxybenzone in acetonitrile. The results are shown in FIG. 1.

Schiff-base formation alters the UV absorption properties in the UV and visible range of the spectrum. FIG. 1 illustrates the absorption properties of oxybenzone can be modulated by reaction with amines to form imines. The hydroxylamine-Schiff base (Imine-3) resulted in a loss in the UVA blocking and reduction in UVB blocking, while Imine-1 and Imine-2 improved both UVA-1, UVA-2, and UVB absorption properties.

Example 2. Synthesis of Carbamate (U.S. Pat. No. 5,490,980)

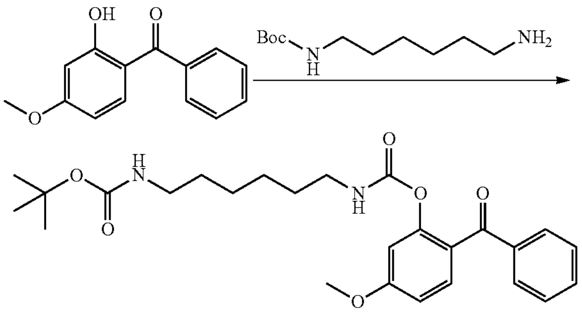

Carbamate-1

U.S. Pat. No. 5,490,980A proposed a transglutaminase-compatible oxybenzone-derived-carbamate functionalized at the phenolic oxygen of oxybenzone with an alkyl-diamine. To assess the UV filter properties of the proposed carbamate, Carbamate-1 was prepared using methods known in the art. However, functionalization at the phenolic oxygen reduces the UV filter properties resulting in reduced UVA blocking.

To a solution of oxybenzone (300 mg, 1.31 mmol, 1 eq) and 4-(dimethylamino)pyridine (DMAP) (161 mg, 1.31 mmol, 1 eq) in dichloromethane (3 mL) was added (4-nitrophenyl) carbonochloridate (265 mg, 1.31 mmol, 1 eq) at 25° C. The reaction was stirred at 25° C. for 2 hrs. N-Boc-1,6-hexanediamine (284 mg, 1.31 mmol, 1 eq) and N-ethyldiisopropylamine (170 mg, 1.31 mmol, 1 eq) were added, and the reaction was stirred 25° C. for 2 hr. The reaction mixture was poured into water (10 mL) and extracted with ethyl acetate (30 mL×3). The combined organic layers were dried over $Mg_2SO_4$ and concentrated. The crude product was purified by reversed-phase HPLC (column: Xtimate C18 150*40 mm*10 μm; mobile phase: [water (HCl)-ACN]; B %: 50%-80%, 10 min) to give Carbamate-1 (165 mg, 26% yield) as white solid, confirmed by LCMS and $^1$H NMR (DMSO).

a. UVA and UVB Absorption Properties.

Figure 2:
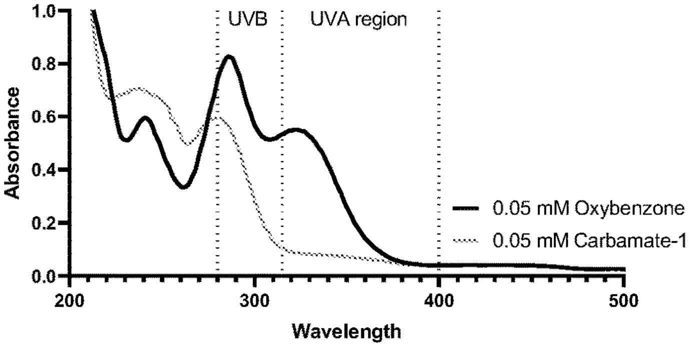
FIG. 2 depicts the UV/Vis spectral properties of Carbamate-1 compared to oxybenzone in acetonitrile.
Figure 2:
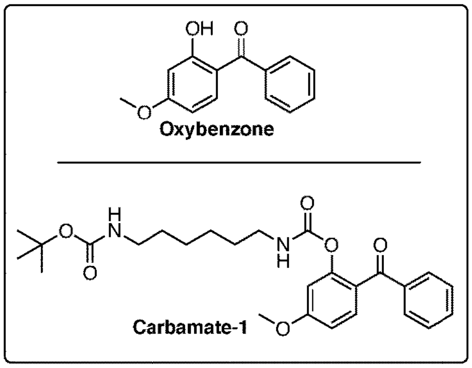

Carbamate-1, first described in U.S. Pat. No. 5,490,980A, was synthesized, purified, and isolated (see above). Carbamate-1 was dissolved in acetonitrile to a final concentration of 0.05 mM and analyzed by UV/Vis (Cary-50 Spectrophotomer). The spectral properties were compared to oxybenzone in acetonitrile at a final concentration of 0.05 mM. The results in FIG. 2 demonstrate that Carbamate-1 (having functionalization at the phenolic oxygen) resulted in reducing the UV filter properties, more specifically, UVA blocking was reduced.

Example 3. Synthesis and Analysis of Oxybenzone Series of Imines, Tgase Substrates a. Synthesis of Imine-4.

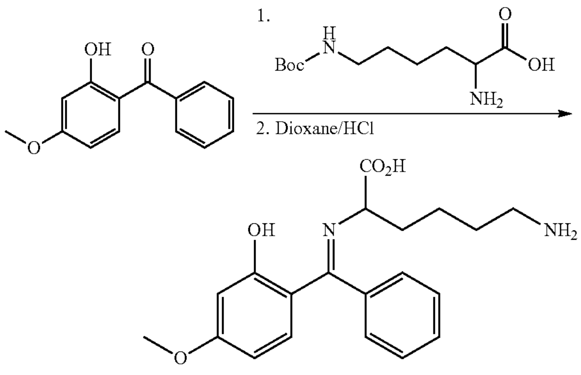

Imine-4

To a solution of oxybenzone (300 mg, 1.31 mmol, 1 eq) and $N_\alpha$-(tert-Butoxycarbonyl)-lysine ($N_\alpha$-Boc-Lysine-OH) (388 mg, 1.58 mmol, 1.2 eq) in methanol (3 mL) was added sodium methoxide (394 μL of 5 M, 1.5 eq) at 25° C. The reaction mixture was heated to 80° C. for 12 hr and monitored by LCMS. The reaction mixture was quenched by dilution into water (20 mL) and extracted with ethyl acetate (30 mL×2). The organic layer was discarded. The aqueous phase was lyophilized to afford the crude product, which was purified by reversed-phase HPLC (column: Xtimate C18 150*40 mm*10 μm; mobile phase: [water(HCl)-ACN]; B %: 30%-60%, 10 min). The N-Boc-Imine-4 (350 mg, 537 μmol, 41% yield) was isolated as green solid, confirmed by LCMS and $^1$H NMR ($CDCl_3$).

To a solution of N-Boc-Imine-4 (350 mg, 767 μmol, 1 eq) in DCM (10 mL) was added HCl/dioxane (1.15 mL of 4 M, 6 eq) at 25° C. The reaction mixture was stirred at 25° C. for 2 hr and monitored by LCMS. The reaction mixture was concentrated in vacuo to give the crude product. The crude product was triturated with ethyl acetate (5 mL) at 25° C. for 30 min and filtered. The filter cake was dried under vacuum to give Imine-4 (139 mg, 46% yield) as yellow solid, confirmed by LCMS and $^1$H NMR (DMSO).

b. Synthesis of Imine-5.

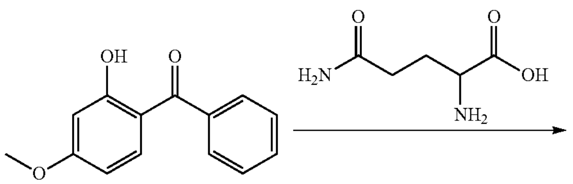

-continued

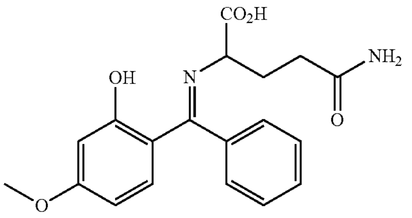

Imine-5

To a solution of oxybenzone (500 mg, 2.19 mmol, 1 eq) and glutamine (384 mg, 2.63 mmol, 1.2 eq) in methanol (5 mL) was added sodium methoxide (876 μL of 5 M, 2 eq) at 25° C. The reaction mixture was heated to 65° C. for 12 hr and monitored by LCMS, which revealed that ~43% of desired product was formed. The suspension was filtered, and the filter cake was washed with methanol (5 mL×3). The combined filtrates were concentrated. The crude product was purified by prep-HPLC and again by SFC (column: DAICEL CHIRALPAK AD (250 mm*30 mm, 10 μm) to give Imine-5 (19 mg, 2% yield) as a gray solid, confirmed by LCMS and $^1$H NMR (DMSO).

c. Synthesis of Imine-6.

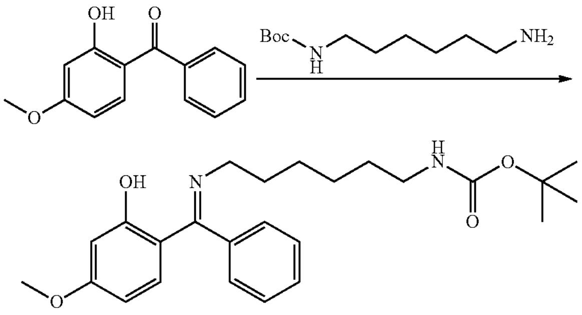

N-Boc-Imine-6

To a solution of oxybenzone (341 mg, 1.58 mmol, 1.2 eq) and N-Boc-1,6-hexanediamine (300 mg, 1.31 mmol, 1 eq) in toluene (3 mL) was added tetraisopropoxytitanium (747.14 mg, 2.63 mmol, 775.84 μL, 2 eq) at 25° C. The reaction mixture was heated to 80° C. for 12 hr and monitored by LCMS. The reaction was quenched by dilution in water (20 mL) and the product was extracted with EtOAc (30 mL×3). The combined organic layers were dried over $Mg_2SO_4$ and concentrated. The residue was purified by column chromatography ($SiO_2$, Ethyl acetate:Petroleum ether=0~30%) to give N-Boc-Imine-6 (450 mg, 80% yield) as yellow oil, confirmed by LCMS.

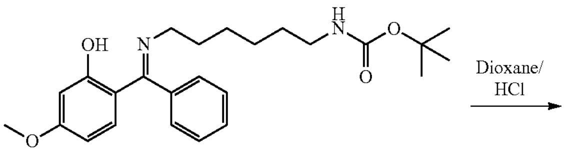

N-Boc-Imine-6

-continued

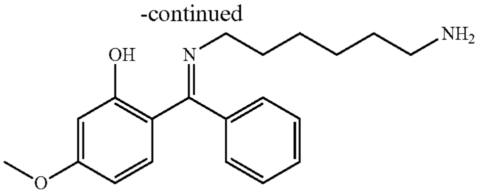

Figure 4:
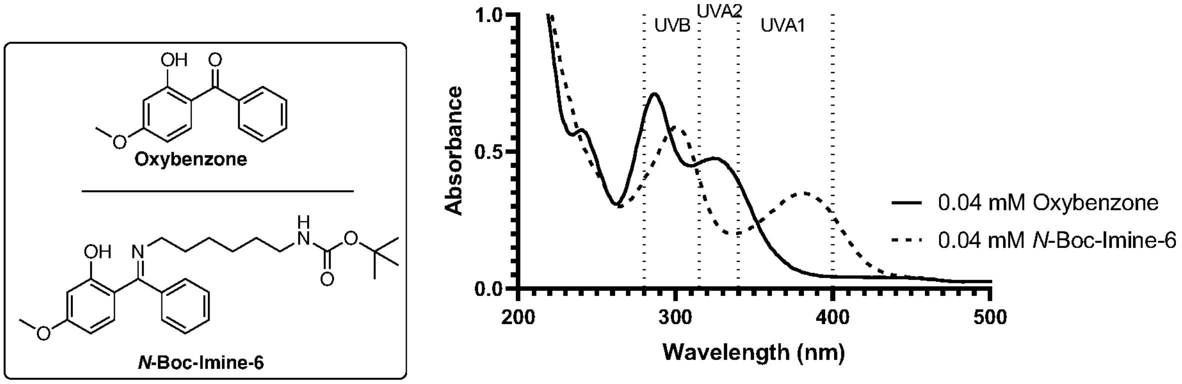
FIG. 4 depicts the UV/Vis spectral properties of N-Boc-Imine-6 in ethanol.

Imine-6 by LCMS indicating completion. The reaction was then diluted in ethanol to final concentration of 0.04 mM and analyzed by UV/Vis spectroscopy. The N-Boc-Imine-6 was stable over 24 hours at high temperature (70° C.) in ethanol without reversion to the starting ketone and amine (FIG. 4). Additionally, the Boc-protecting group remained intact throughout the reaction and UV/Vis analysis. The results in FIG. 4 show that absorption of N-Boc-Imine 6 encompasses the UVA and UVB regions as well as the visible region of the spectrum (greater than 400 nm).

Example 4. Synthesis and Analysis of Avobenzone-Imine, Imine-7

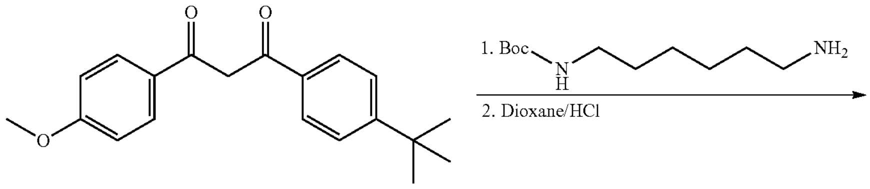

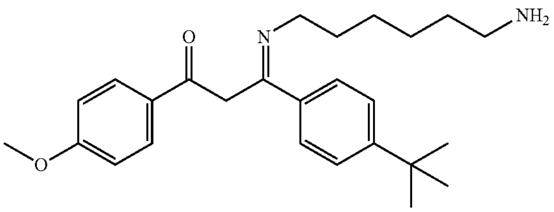

Imine-7

To a solution of N-Boc-Imine-6 (450 mg, 1.05 mmol, 1 eq) in dichloromethane (10 mL) was added HCl/dioxane (4 M, 1.32 mL, 5 eq). The reaction stirred at 25° C. for 2 hr and was monitored by LCMS. The reaction was concentrated in vacuo to give Target 6 (95 mg, 27% yield) as green oil, confirmed by LCMS and $^1$H NMR (DMSO).

d. UVA and UVB Absorption Properties.

Figure 3:
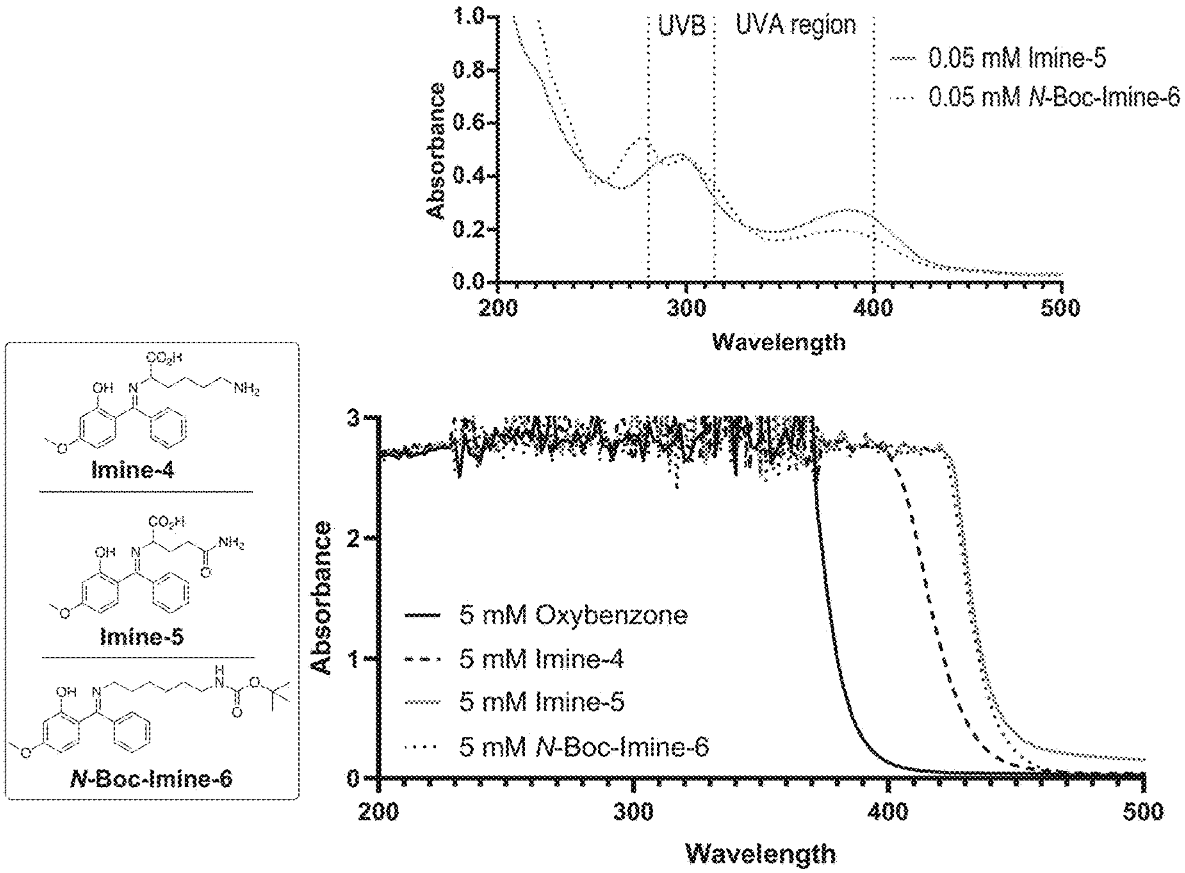
FIG. 3 depicts the UV/Vis spectral properties of Imine-4, Imine-5, and N-Boc-Imine-6 compared to oxybenzone in acetonitrile.

Imine-4, Imine-5, and N-Boc-Imine-6 were synthesized, purified, and isolated (see above). All three compounds were separately dissolved in acetonitrile to a final concentration of 5 mM (FIG. 3) and analyzed by UV/Vis (Cary-50 Spectrophotomer). N-Boc-Imine-6 was diluted in acetonitrile to a final concentration of 0.05 mM (FIG. 3, inset) and analyzed by UV/Vis. The N-Boc-Imine-6 was utilized for this data, instead of Imine-6, due to poor solubility of Imine-6 in acetonitrile. Spectral properties were compared to oxybenzone in acetonitrile at the same concentration. FIG. 3 depicts the absorption spectra of the three imines derived from oxybenzone and shows that the three imines encompassed the UVA-1, UVA-2, and UVB regions as well as the visible region of the spectrum (greater than 400 nm).

To understand the solution stability of the Boc-protected imines in protic solvent, N-Boc-Imine-6 was prepared in ethanol in the presence of catalytic glacial acetic acid. Briefly, to a solution of oxybenzone (0.10 g, 0.438 mmol, 1 eq) and N-Boc-1,6-hexanediamine (0.094 g, 0.43 mmol, 1 eq) in ethanol (0.3 mL) was added catalytic glacial acetic acid (1 μL). The reaction mixture was agitated at 900 rpm at 70° C. for 16 hr and monitored by LCMS. Full reaction of the starting material to a single product peak was observed To a solution of avobenzone (2 g, 6.44 mmol, 1 eq) and N-Boc-1,6-hexanediamine (1.39 g, 6.44 mmol, 1 eq) in toluene (80 mL) was added 4A molecular sieves (2 g, 9.90 mmol, 1.54 eq), followed by Amberlyst® 15 hydrogen form (2 g, 6.37 mmol) at 25° C. under $N_2$. After addition, the reaction mixture was stirred at 110° C. for 72 hr and monitored by LCMS. The suspension was filtered, and the filter cake was washed with DCM (20 mL×3). The combined filtrate was concentrated. The residue was purified by column chromatography (SiO2, ethyl acetate:Petroleum ether=0 to 25%). N-Boc-Imine-7 (1.09 g, 1.99 mmol, ~30% yield) was obtained as yellow oil, confirmed by LCMS and 1H NMR (CDCl3).

To a solution of N-Boc-Imine-7 (300 mg, 590 μmol, 1 eq) in DCM (6 mL) was added HCl/dioxane (4 M, 737 μL, 5 eq) at 25° C. under $N_2$. After addition, the reaction mixture was stirred at 25° C. for 4 hr and monitored by LCMS. The mixture was concentrated to dryness, Imine-7 (150 mg, 332 μmol, ~50% yield) was obtained as yellow oil, confirmed by LCMS and $^1$H NMR (DMSO).

UVA and UVB Absorption Properties.

Figure 5:
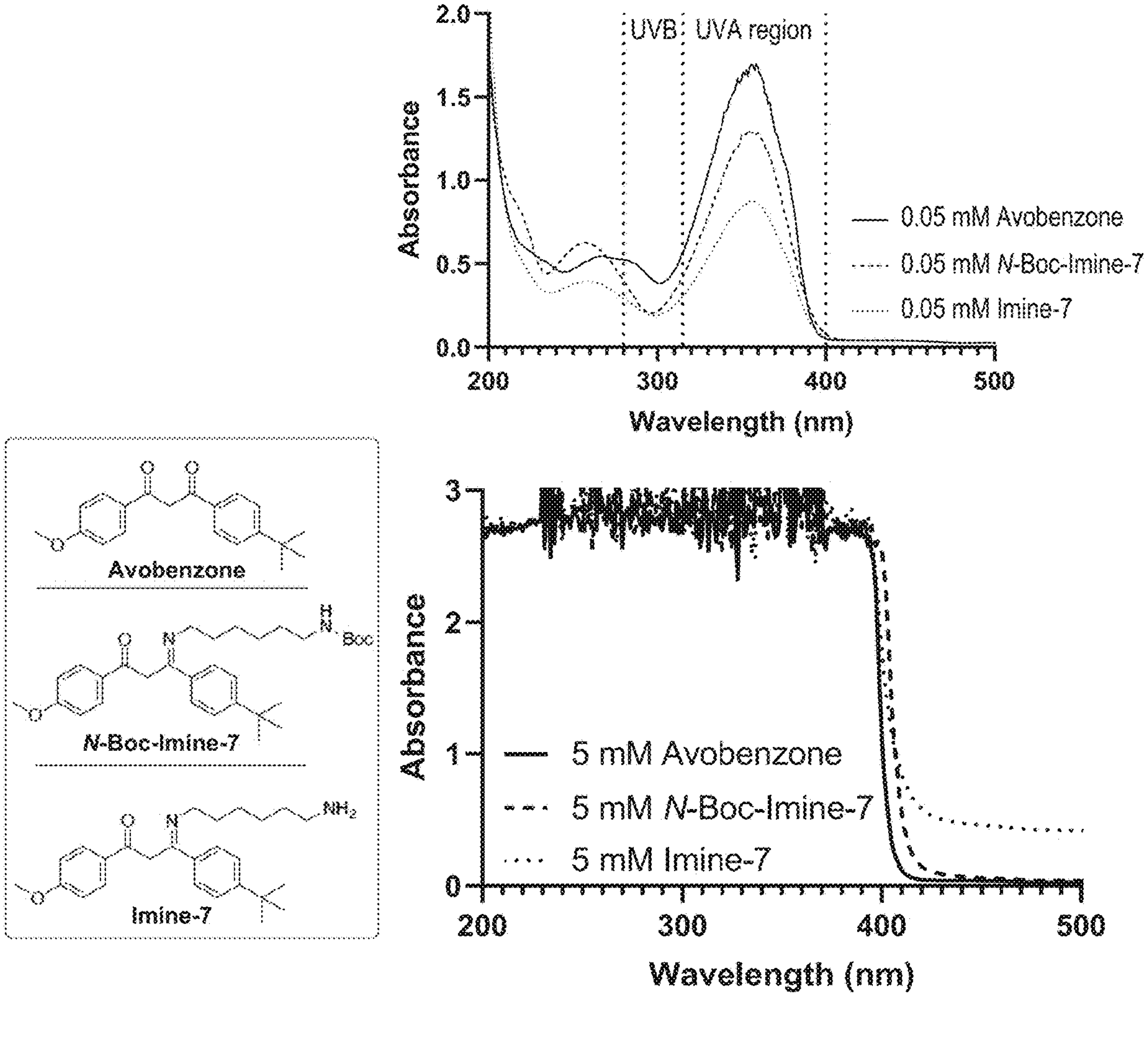
FIG. 5 depicts the UV/Vis spectral properties of Imine-7 and N-Boc-Imine-7 compared to avobenzone in acetonitrile.

Imine-7 and N-Boc-Imine-7 were synthesized, purified, and isolated using preparative HPLC (see above). Imine-7 and N-Boc-Imine-7 were dissolved in acetonitrile to an estimated concentration of 5 mM (FIG. 5) and 0.05 mM (FIG. 5, inset). Both solutions were analyzed by UV/Vis (Cary-50 Spectrophotomer). The concentration of Imine-7 and N-Boc-Imine-7 (0.05 mM) is an estimation, and the absorbance signal is lower than would be expected. The low purity of the compounds is likely due to additional salt from HPLC purification and presence of residual t-butanol (confirmed by NMR). Spectral properties were compared to avobenzone in acetonitrile for qualitative purposes only as the extinction coefficient are likely equal to or greater than unfunctionalized avobenzone. The results are shown in FIG. 5.

Example 5. Synthesis and Analysis of Sulisobenzone Derived Imine, Tgase Substrate

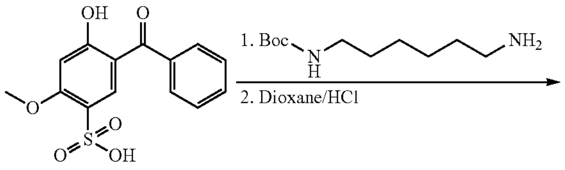

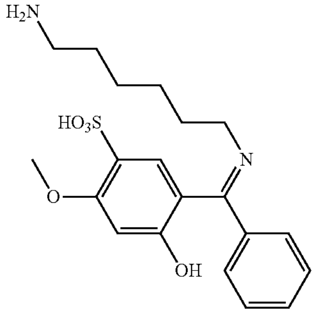

Imine-8

To a solution of sulisobenzone (0.10 g, 0.32 mmol, 1 eq) and N-Boc-1,6-hexanediamine (0.070 g, 0.32 mmol, 1 eq) in ethanol (0.3 mL) was catalytic glacial acetic acid (1 μL). After addition, the reaction mixture was stirred at 70° C. for 16 hr and monitored by LCMS. The N-Boc-Imine-8 was concentrated and used without further purification. LCMS showed a single peak with m/z of 506, 407, and 432.

N-Boc-Imine-8 (0.32 μmol, 1 eq) in DCM (6 mL) is treated with HCl/dioxane (4 M, 737 μL, 5 eq) at 25° C. for 4 hrs. The mixture is concentrated, and Imine-8 is obtained.

Alternatively, Imine-8 was prepared directly by reaction of sulisobenzone (1 eq) with 1-6-hexamethylene diamine (1 eq) in refluxing ethanol.

UVA and UVB Absorption Properties.

Figure 6:
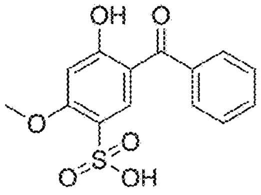
FIG. 6 depicts the UV/Vis spectral properties of N-Boc-Imine-8 and Imine-8 compared to sulisobenzone in ethanol at about equal concentration.
Figure 6:
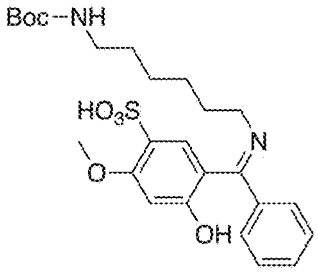
Figure 6:
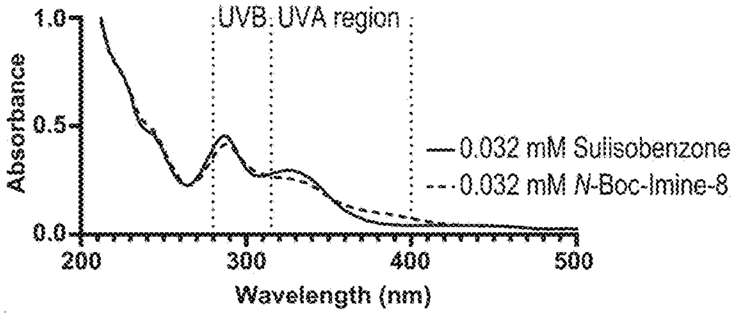
Figure 6:
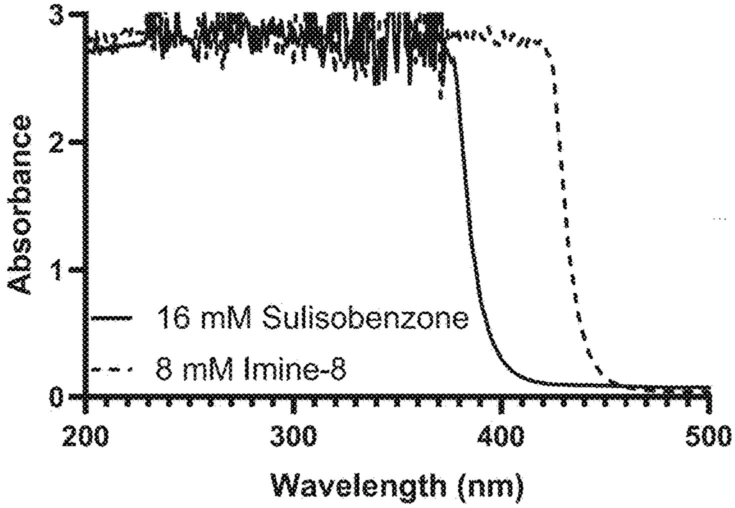

N-Boc-Imine-8 and Imine-8 was synthesized, purified, and isolated (see above). N-Boc-Imine-8 and Imine-8 were dissolved in ethanol to a final concentration of 0.032 mM and 8 mM, respectively (FIG. 6) and analyzed by UV/Vis. (Cary-50 Spectrophotomer). Spectral properties were compared to sulisobenzone in ethanol at similar concentration. The results in FIG. 6 show that N-Boc-Imine-8 and Imine-8 retained absorbance in the UVB region and extended absorbance into the UVA region.

Example 6. Synthesis and Analysis of Diethylamino Hydroxybenzoyl Hexyl Benzoate Derived Imine, Tgase Substrate

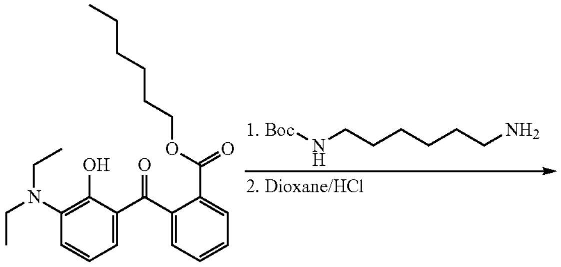

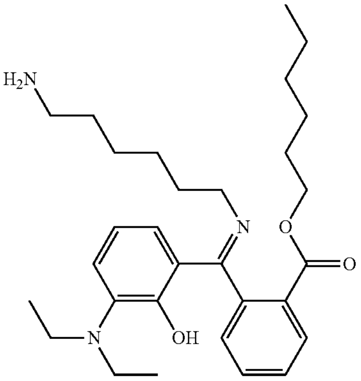

Imine-9

To a solution of diethylamino hydroxybenzoyl hexyl benzoate (DHHB) (0.10 g, 0.25 mmol, 1 eq) and N-Boc-1,6-hexanediamine (0.070 g, 0.32 mmol, 1 eq) in toluene (0.3 mL) was catalytic glacial acetic acid (1 μL). After addition, the reaction mixture was stirred at 95° C. for 16 hr and monitored by LCMS. The reaction was concentrated and used without further purification to yield a deep orange oil. LCMS showed a single peak with m/z of 595 and 495.

N-Boc-Imine-9 (0.32 μmol, 1 eq) in DCM (6 mL) is treated with HCl/dioxane (4 M, 737 μL, 5 eq) at 25° C. for 4 hrs. The mixture is concentrated, and Imine-9 is obtained. Alternatively, Imine-9 was prepared directly by reaction of DHHB (1 eq) with 1-6-hexamethylene diamine (1 eq) in refluxing ethanol. Both N-Boc-Imine-9 and Imine-9 result in a red shift of the absorbance spectra, which extends to the visible region (data not shown).

Example 7. Synthesis and Analysis of Oxybenzone Imine on a High Molecular Weight Polymer

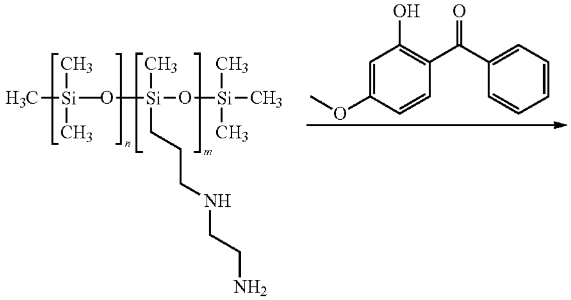

-continued

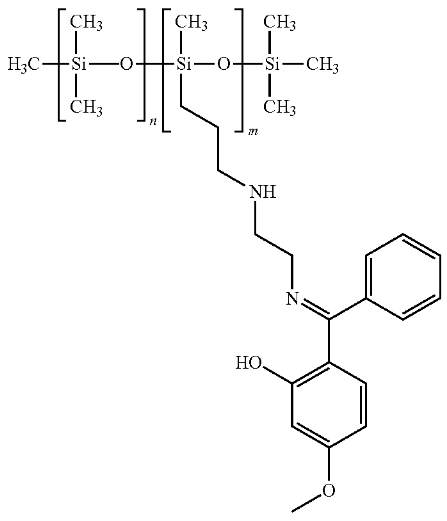

Imine-10

To oxybenzone (100.0 mg, 0.44 mmol, 1 eq) was added amodimethicone (910.0 mg, 0.55 mmol, 1.2 eq) at 25° C. The reaction mixture was heated to 95° C. for 16 hr with continuous mixing. On heating, the oxybenzone melted, forming an immiscible phase at the bottom of the vial. As the reaction progressed, the oxybenzone phase shrunk and the amodimethicone phase took on a clear, yellow color. Imine-10 was obtained by allowing the reaction to continue until a single, clear yellow phase in the vial. The high molecular weight imine polymer described in this example has an increased absorbance in the UVA range as well as the visible range (FIG. 7) and avoids skin penetration due to its high molecular weight. It is believed that Imine-10 will have water resistant properties owing to the hydrophobic nature of the silicone backbone.

UVA and UVB Absorption Properties.

Figure 7:
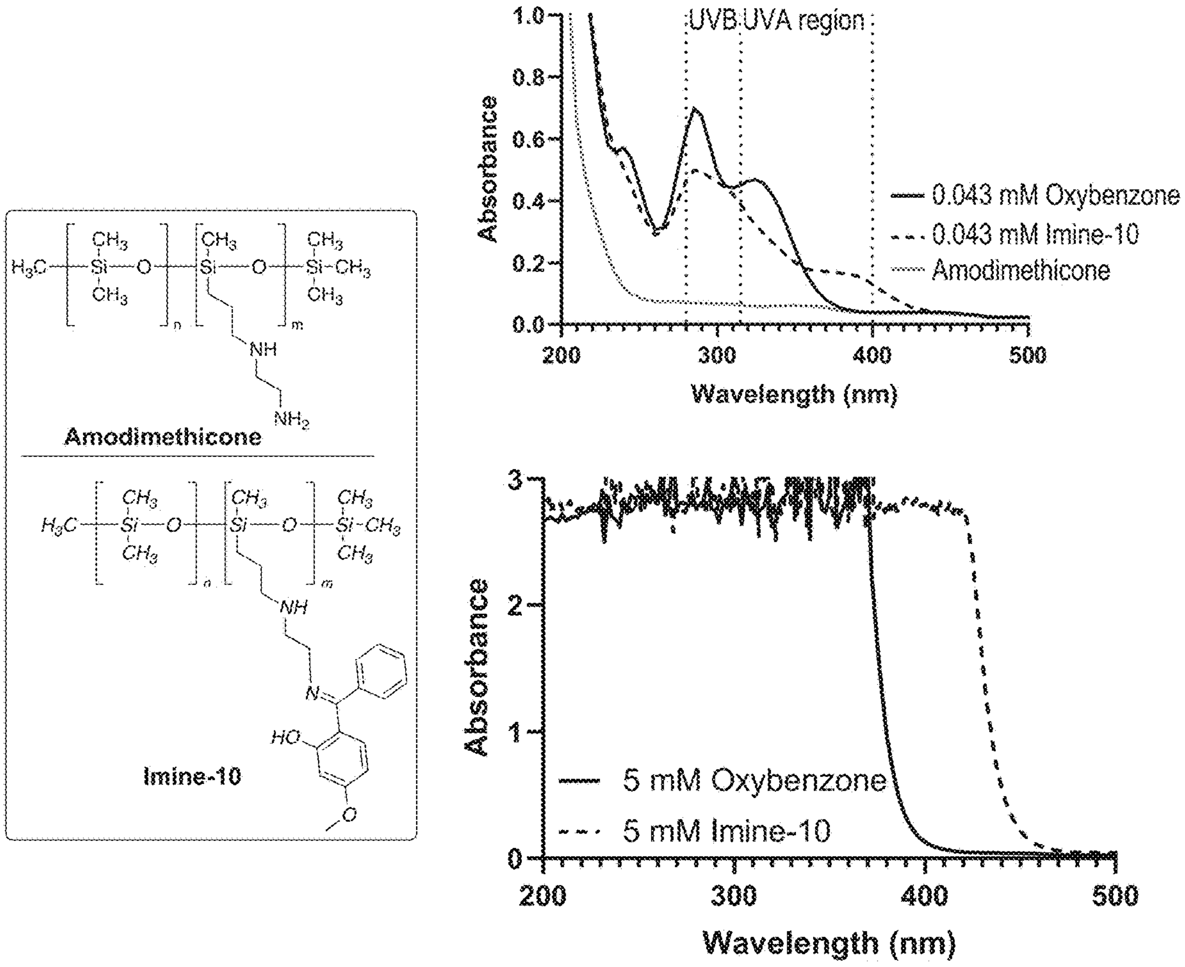
FIG. 7 depicts the UV/Vis spectral properties of Imine-10 in ethanol.

Imine-10 was first dissolved in methyl tert-butyl ether and then diluted in ethanol to a final concentration of 5 mM and 0.04 mM (FIG. 7) and analyzed by UV/Vis. (Cary-50 Spectrophotomer). Spectral properties were compared to oxybenzone at similar concentration. The results in FIG. 7 show that Imine-10 retains absorbance in the UVB region and extended absorbance into the UVA and visible region.

Example 8. Covalent Addition of Sunscreen-Linker to Peptide

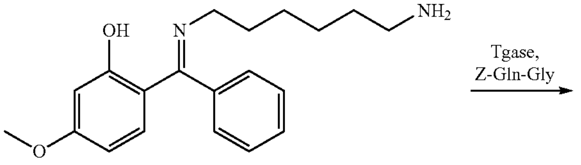

Imine-6

-continued

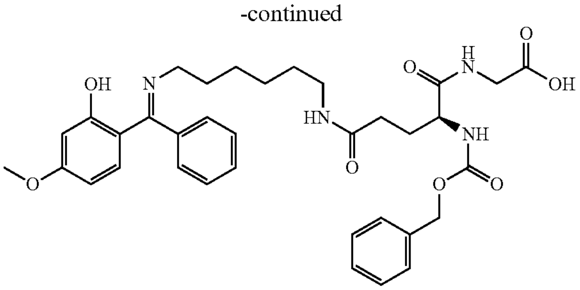

Cbz-Gln-Gly dipeptide (100 μL of 10 g/L stock solution dissolved in 90% acetonitrile in water) was added to a solution of wild-type transglutaminase or a variant (SEQ ID NO: 2 and 7) in 0.1 M Tris-HCl pH 8.0, 1 mM EDTA (800 μL, 0.03 g/L final concentration). To this solution was added the imine products described in Examples 3-6 dissolved in a suitable solvent (100 μL of 10 g/L stock solution dissolved in solvent identified in table 2). The suspensions were incubated at 37° C. overnight with constant agitation. Transglutaminase (wild-type or variant) catalyzed, covalent addition of the dipeptide to the imine was confirmed by HPLC and LCMS. Conversion of starting material to product was calculated using peak areas. Relative reactivity is calculated by dividing all conversions by the data obtained for the least reactive imine. In the absence of transglutaminase, no covalent addition of the imine to the peptide was observed. Reactivity of the imine was dependent of the imine's solubility upon addition to the aqueous reaction. The more water-soluble imines afford higher conversion to the imine-peptide product.

TABLE 2

Enzyme catalyzed covalent addition of imines to target of interest.

| Imine-UV filter | Solvent used for dissolution | Relative Reactivity |
|---|---|---|
| Imine-6 | 1:1 dichloromethane to acetonitrile | 1× |
| Imine-8 | Suspension in water | 8× |
| Imine-9 | Ethanol | 10× |

Example 9. Sunscreen Composition Formulation

A sunscreen composition comprising any of the UV filters described herein may be formulated as set forth in Table 3. The below described formulation is suitable for both oil-in-water emulsions and water-in-oil emulsions.

TABLE 3

Sunscreen Formulation

| Function | Chemical Properties | w/w % Range |
|---|---|---|
| Water | Water | 40.0-60.0% |
| Emulsifier | Glyceryl Esters, Polyethylene Glycol Ethers of fatty alcohols, Glutamate derivatives, Glycoside (C8-C20), Alkyl Sulfates, amino acid salts, esters and acyl derivatives, Glycosaminoglycans and its derivatives, | 0.01-10% |
| Humectant | Diols, triols, polyols | 1.0-10.0% |
| Emollient, | Hydrocarbons (C3-C16 linear and its | 2.0-20.0% |

TABLE 3-continued

| Sunscreen Formulation | | |
|---|---|---|
| Function | Chemical Properties | w/w % Range |
| liquid | isomers) and polymers thereof, Esters (C6-C34, branched or linear), such as carbonates, isononanoates, caprylates, oleates, adipates, stearates, myristates, laurates, benzoates, maleates, pentanoates, hexanoates, heptanoates | |
| Emollient, solid | Fatty Alcohol (C12-C20) such as cetyl-, stearyl-, cetearyl-, behenyl-, fatty esters such as distearates, palmitates, myristates, stearates, laurates | 0.01-10.0% |
| Thickener | Polysaccharide (corn sugar, cellulose, agar, carrageenan, starches), acrylates (carbomers, co- and crosspolymers, salts), Inorganic Salts (silicates), Inorganic Clays (bentonite and its derivatives) | 0.01-10% |
| Preservative | Any cosmetically acceptable preservative | 0.001-1.0% |
| Chelating Agent | EDTA and its derivatives | 0.001-1.0% |
| UV filters | Avobenzone, salicylates, cinnamates, benzophenones, ensulizole, triazine or any of the imine/enamine UV filters described herein | 1.0-20% |

Example 10. Determination of Water Resistance of Sunscreens

In vitro Testing Methodology (based on method of Markovic et al, Alured's Cosmetics and Toiletries, 116(9):61-28 (2001):

Before application of sunscreens, large strips (20×10 cm) of collagen-based synthetic skin substrate formulated to mimic human skin, sold under the trademark of Vitro-Skin® N-19 (IMS, Inc.), are hydrated following the manufacturer's recommendations (16-18 hours at 90-95% relative humidity at room temperature). Vitro-Skin© simulates the properties of composition, wettability, pH, ionic strength, and surface topography of human skin. A measured amount (6-7 mg) of formulation containing an imine or enamine as described herein is applied on pre-hydrated pieces of Vitro-Skin® (28×38 mm) that are mounted in 35 mm slide mounts. The emulsion is carefully spread using a rubber-gloved finger with initial circular and then linear motion for approximately one minute. Samples are then placed in a humidity chamber (90-95% relative humidity at room temperature) for 20 minutes to allow for emulsion coalescence. Four UV spectra are collected per sample in the wavelength range of 250-350 nm using a spectrophotometer. Each spectrum is collected after a 900 rotation of the sample giving four separate area scans for each sample. Samples are scanned against the untreated reference sample in the reference beam of the two-beam spectrophotometer. Absorbance readings are taken at 310 and 291 nm and are labeled as the initial absorbance, Ai. Samples are then immersed in a temperature-controlled water bath (25±0.2° C.) for 80 minutes with constant mixing using a paddle type impeller at 50 rpm. The volume of the water bath is large enough (2000 ml) to prevent a high concentration of dispersed sunscreen and possibility of re-adsorption. After immersion, the samples are taken out of the water, lightly shaken to remove the largest water droplets and are hung in the air in a climate-controlled room at 50% relative humidity for 30 minutes. Afterward, the samples are placed back into the humidity chamber for 120 minutes. Final absorbance readings, Af, are taken in the same manner as the initial ones. The percentage of water resistance is calculated as (Af/AI)×100. Samples are run in quadruplicates giving 32 readings (4 samples×4 orientations×2 wavelengths) for each formulation that is tested. It is important that the samples remain hydrated; if they lose too much moisture, the Vitro-Skin® becomes opaque and unsuitable for spectrophotometric analysis. Each blank control sample (without sunscreen) is treated and is measured in exactly the same way. The control sample is immersed in a separate water bath, to ensure no sunscreen transfer from formulation-treated samples.

Example 11. Tgase Vector Construction and Mutagenesis

Cell Free Protein Synthesis (CFPS) Vectors

The genes coding for the pro-sequence and mature Tgase were codon optimized for expression in *E. coli* based on the published amino acid sequence (Kanaji, et al. (1993) J. Biol. Chem. 268(16):11565-11572), synthesized, and cloned onto pUC19-derived expression vectors as described in PCT/US20/49226.

*E. coli* Vector

The genes coding for the pro-sequence and mature Tgase were codon optimized for expression in *E. coli* based on the published amino acid sequence (Kanaji, et al. (1993) *J. Biol. Chem.* 268(16):11565-11572) and synthesized as described in PCT/US20/49226. The DNA was cloned onto the pET9a vector under control of the T7 promoter for expression in *E. coli.*

Creation of Tgase variants

Mutations were introduced into the mature Tgase gene using site directed mutagenesis methods known in the art.

Example 12. Expression of Tgase Variants Using Cell-Free Protein Synthesis

Pro-sequence and mature Tgase variants were expressed simultaneously in a commercially available cell-free protein synthesis kit following the manufacturer's instructions as described in PCT/US20/49226.

Example 13. Expression and Purification of Tgase Variants in *E. coli*

*E. coli* BL21(DE3) cells harboring the Tgase expression plasmid were grown in shake flasks, lysed by homogenization, and the Tgase was isolated from the cell debris by centrifugation. The resulting semi-purified enzyme (clarified lysate) was further purified by affinity column on a Ni-IMAC resin prior to dialysis. Purified Tgase was stored at −80° C.

Example 14. Measurement of Tgase Specific Activity

Tgase specific activity was measured in the examples herein using a colorimetric hydroxamate activity assay (Folk and Cole (1965) *J Biol Chemistry* 240(7):2951-2960). Briefly, the hydroxamate assay uses N-carbobenzoxy-L-glutaminylglycine (Z-Gln-Gly or CBZ-Gln-Gly) as the amine acceptor substrate and hydroxylamine as an amine donor. In the presence of transglutaminase, the hydroxylamine is incorporated to form Z-glutamylhydroxamate-glycine, which develops a colored complex with iron (III), detectable at 525 nm after incubation at 37° C. for 5-60 minutes. The calibration was performed using L-glutamic acid 7-monohydroxamate (Millipore Sigma) as standard. One unit of Tgase is defined as the amount of enzyme that catalyzes formation of 1 μmol of the peptide derivative of 7-glutamylhydroxylamine per minute.

All publications, patents, and patent applications cited herein are hereby incorporated by reference in their entireties for all purposes and to the same extent as if each individual publication, patent, or patent application were specifically and individually indicated to be so incorporated by reference.

| Amino Acid Sequences |
|---|
| SEQ ID NO: 1 Wild-Type Tgase from *Streptomyces mobaraensis*<br>DSDDRVTPPAEPLDRMPDPYRPSYGRAETVVNNYIRKWQQVYSHRDGRK<br>QQMTEEQREWLSYGCVGVTWVNSGQYPTNRLAFASFDEDRFKNELKNGR<br>PRSGETRAEFEGRVAKESFDEEKGFQRAREVASVMNRALENAHDESAYL<br>DNLKKELANGNDALRNEDARSPFYSALRNTPSFKERNGGNHDPSRMKAV<br>IYSKHFWSGQDRSSSADKRKYGDPDAFRPAPGTGLVDMSRDRNIPRSPT<br>SPGEGFVNFDYGWFGAQTEADADKTVWTHGNHYHAPNGSLGAMHVYESK<br>FRNWSEGYSDFDRGAYVITFIPKSWNTAPDKVKQGWP |
| SEQ ID NO: 2 N282E H289I S299K<br>DSDDRVTPPAEPLDRMPDPYRPSYGRAETVVNNYIRKWQQVYSHRDGRK<br>QQMTEEQREWLSYGCVGVTWVNSGQYPTNRLAFASFDEDRFKNELKNGR<br>PRSGETRAEFEGRVAKESFDEEKGFQRAREVASVMNRALENAHDESAYL<br>DNLKKELANGNDALRNEDARSPFYSALRNTPSFKERNGGNHDPSRMKAV<br>IYSKHFWSGQDRSSSADKRKYGDPDAFRPAPGTGLVDMSRDRNIPRSPT<br>SPGEGFVNFDYGWFGAQTEADADKTVWTHGNHYHAPEGSLGAMIVYESK<br>FRNWKEGYSDFDRGAYVITFIPKSWNTAPDKVKQGWP |
| SEQ ID NO: 3 N282K G283A S284P S299V<br>DSDDRVTPPAEPLDRMPDPYRPSYGRAETVVNNYIRKWQQVYSHRDGRK<br>QQMTEEQREWLSYGCVGVTWVNSGQYPTNRLAFASFDEDRFKNELKNGR<br>PRSGETRAEFEGRVAKESFDEEKGFQRAREVASVMNRALENAHDESAYL<br>DNLKKELANGNDALRNEDARSPFYSALRNTPSFKERNGGNHDPSRMKAV<br>IYSKHFWSGQDRSSSADKRKYGDPDAFRPAPGTGLVDMSRDRNIPRSPT<br>SPGEGFVNFDYGWFGAQTEADADKTVWTHGNHYHAPKAPLGAMHVYESK<br>FRNWVEGYSDFDRGAYVITFIPKSWNTAPDKVKQGWP |
| SEQ ID NO: 4 S199A S299A<br>DSDDRVTPPAEPLDRMPDPYRPSYGRAETVVNNYIRKWQQVYSHRDGRK<br>QQMTEEQREWLSYGCVGVTWVNSGQYPTNRLAFASFDEDRFKNELKNGR<br>PRSGETRAEFEGRVAKESFDEEKGFQRAREVASVMNRALENAHDESAYL<br>DNLKKELANGNDALRNEDARSPFYSALRNTPSFKERNGGNHDPSRMKAV<br>IYAKHFWSGQDRSSSADKRKYGDPDAFRPAPGTGLVDMSRDRNIPRSPT<br>SPGEGFVNFDYGWFGAQTEADADKTVWTHGNHYHAPNGSLGAMHVYESK<br>FRNWAEGYSDFDRGAYVITFIPKSWNTAPDKVKQGWP |
| SEQ ID NO: 5 S199A S299V<br>DSDDRVTPPAEPLDRMPDPYRPSYGRAETVVNNYIRKWQQVYSHRDGRK<br>QQMTEEQREWLSYGCVGVTWVNSGQYPTNRLAFASFDEDRFKNELKNGR<br>PRSGETRAEFEGRVAKESFDEEKGFQRAREVASVMNRALENAHDESAYL<br>DNLKKELANGNDALRNEDARSPFYSALRNTPSFKERNGGNHDPSRMKAV<br>IYAKHFWSGQDRSSSADKRKYGDPDAFRPAPGTGLVDMSRDRNIPRSPT<br>SPGEGFVNFDYGWFGAQTEADADKTVWTHGNHYHAPNGSLGAMHVYESK<br>FRNWVEGYSDFDRGAYVITFIPKSWNTAPDKVKQGWP |
| SEQ ID NO: 6 S2P S199G S299V<br>DPDDRVTPPAEPLDRMPDPYRPSYGRAETVVNNYIRKWQQVYSHRDGRK<br>QQMTEEQREWLSYGCVGVTWVNSGQYPTNRLAFASFDEDRFKNELKNGR<br>PRSGETRAEFEGRVAKESFDEEKGFQRAREVASVMNRALENAHDESAYL<br>DNLKKELANGNDALRNEDARSPFYSALRNTPSFKERNGGNHDPSRMKAV<br>IYGKHFWSGQDRSSSADKRKYGDPDAFRPAPGTGLVDMSRDRNIPRSPT<br>SPGEGFVNFDYGWFGAQTEADADKTVWTHGNHYHAPNGSLGAMHVYESK<br>FRNWVEGYSDFDRGAYVITFIPKSWNTAPDKVKQGWP |
| SEQ ID NO: 7 S2P<br>DPDDRVTPPAEPLDRMPDPYRPSYGRAETVVNNYIRKWQQVYSHRDGRK<br>QQMTEEQREWLSYGCVGVTWVNSGQYPTNRLAFASFDEDRFKNELKNGR<br>PRSGETRAEFEGRVAKESFDEEKGFQRAREVASVMNRALENAHDESAYL<br>DNLKKELANGNDALRNEDARSPFYSALRNTPSFKERNGGNHDPSRMKAV<br>IYSKHFWSGQDRSSSADKRKYGDPDAFRPAPGTGLVDMSRDRNIPRSPT<br>SPGEGFVNFDYGWFGAQTEADADKTVWTHGNHYHAPNGSLGAMHVYESK<br>FRNWSEGYSDFDRGAYVITFIPKSWNTAPDKVKQGWP |
| SEQ ID NO: 8 Wild-Type Tgase with polyhistidine tag.<br>DSDDRVTPPAEPLDRMPDPYRPSYGRAETVVNNYIRKWQQVYSHRDGRK<br>QQMTEEQREWLSYGCVGVTWVNSGQYPTNRLAFASFDEDRFKNELKNGR<br>PRSGETRAEFEGRVAKESFDEEKGFQRAREVASVMNRALENAHDESAYL<br>DNLKKELANGNDALRNEDARSPFYSALRNTPSFKERNGGNHDPSRMKAV<br>IYSKHFWSGQDRSSSADKRKYGDPDAFRPAPGTGLVDMSRDRNIPRSPT<br>SPGEGFVNFDYGWFGAQTEADADKTVWTHGNHYHAPNGSLGAMHVYESK<br>FRNWSEGYSDFDRGAYVITFIPKSWNTAPDKVKQGWPLEHHHHHH |

What is claimed is:

1. A sunscreen composition comprising an imine analog of a ketone-containing UV filter, wherein the imine analog is selected from:

Imine-1

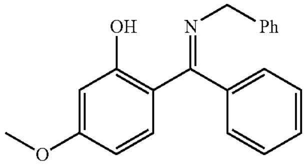

Imine-2

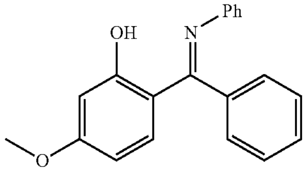

Imine-3

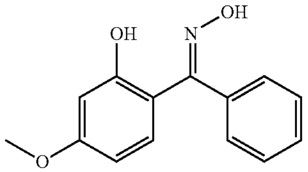

Imine-4

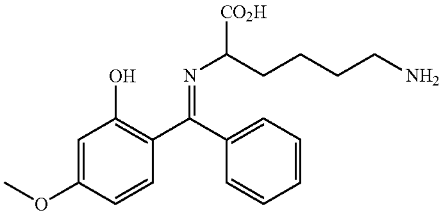

-continued

Imine-5

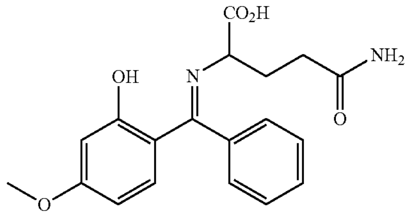

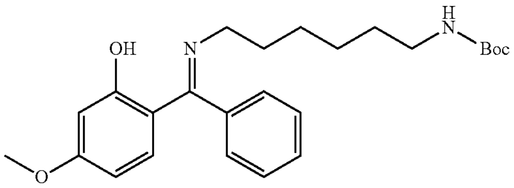

N-(tert-butoxycarbonyl)-Imine-6 (N-Boc-Imine-6)

Imine-6

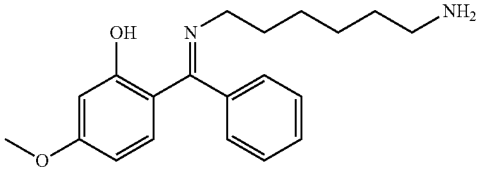

Dimer-Imine-6

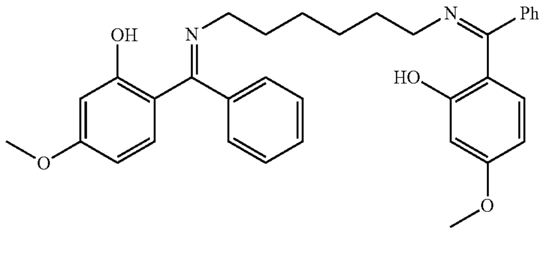

-continued

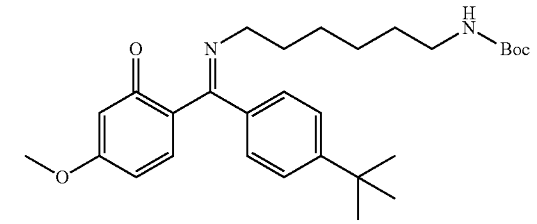

N-(tert-butoxycarbonyl)-Imine-7 (N-Boc-Imine-7)

Imine-7

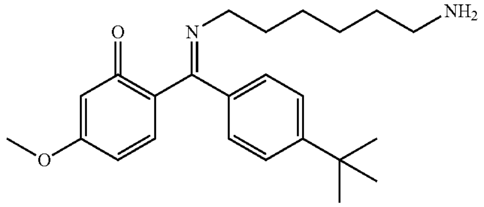

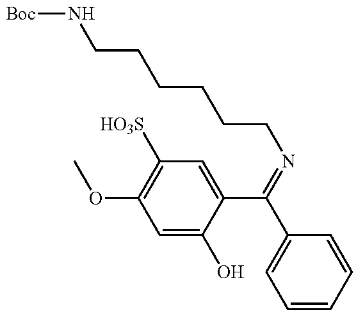

N-(tert-butoxycarbonyl)-Imine-8 (N-Boc-Imine-8)

Imine-8

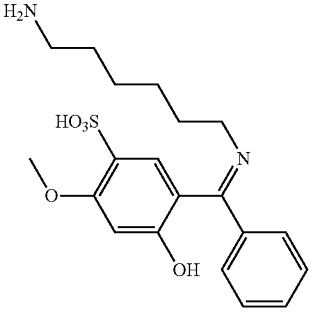

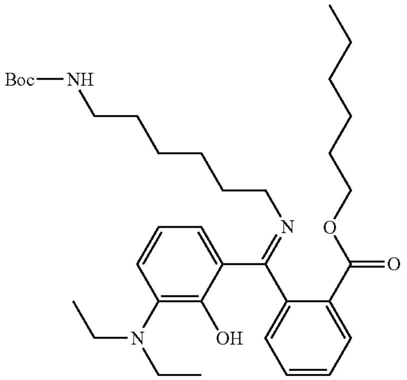

N-(tert-butoxycarbonyl)-Imine-9 (N-Boc-Imine-9)

-continued

Imine-9

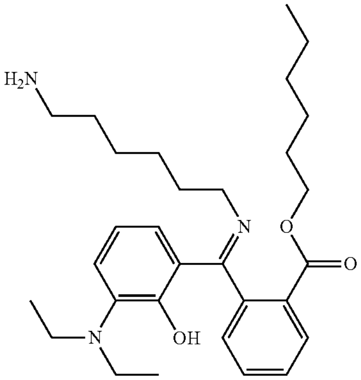

and

Imine-10

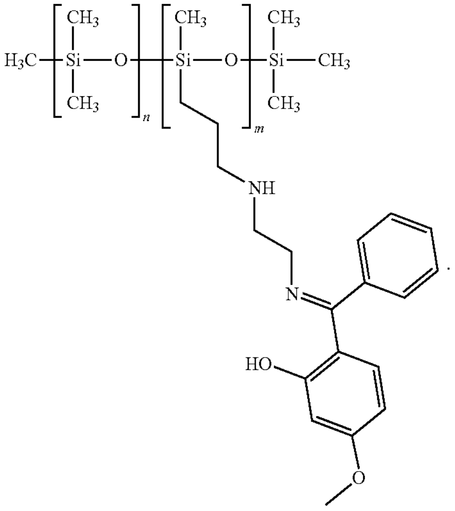

2. The sunscreen composition of claim 1, further comprising a transglutaminase or variant thereof and/or a lysyl oxidase.

3. A sunscreen active ingredient, wherein the sunscreen active ingredient is an imine analog of a ketone-containing UV filter selected from the group consisting of Imine-1

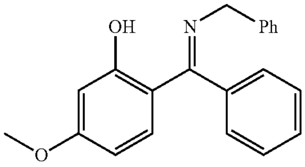

Imine-2

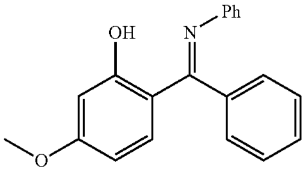

-continued
Imine-3
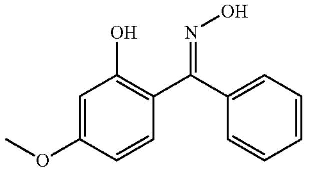
Imine-4
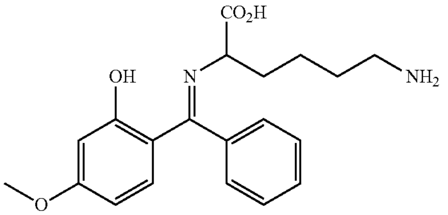
Imine-4
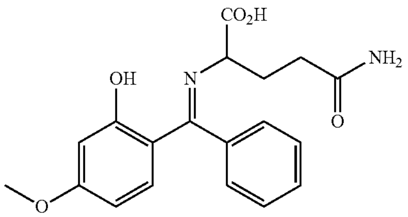
N-Boc-Imine-6
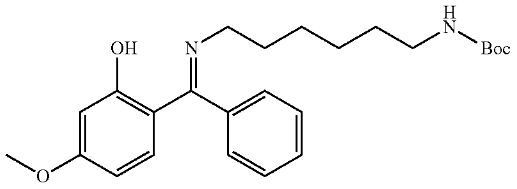
Imine-6
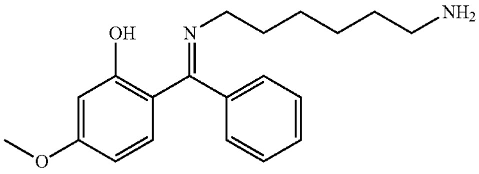
Dimer-Imine-6
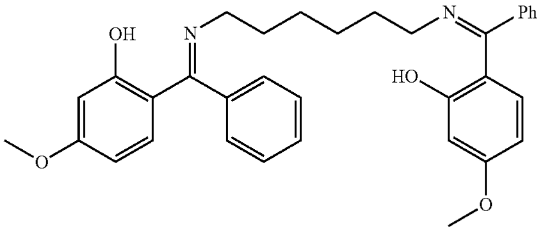
N-Boc-Imine-7
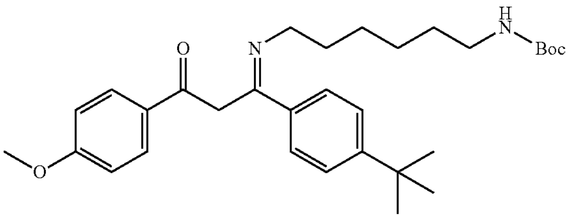
-continued
Imine-7
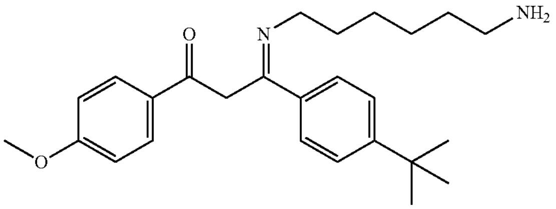
N-Boc-Imine-8
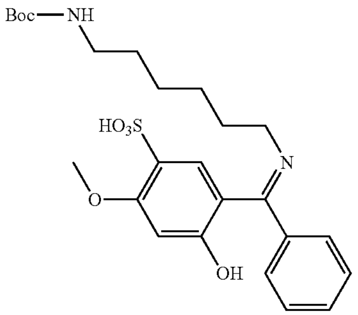
Imine-8
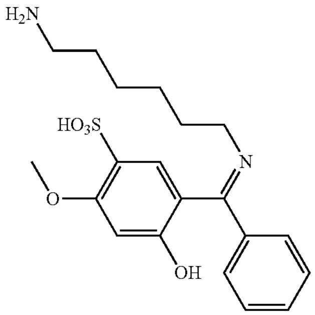
N-Boc-Imine-9
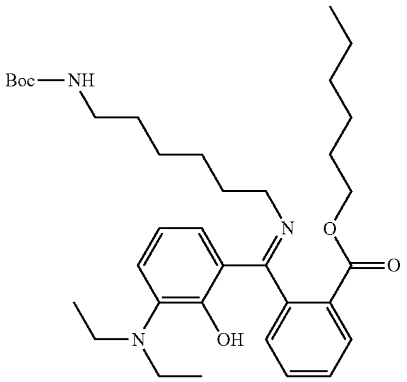

-continued
Imine-9
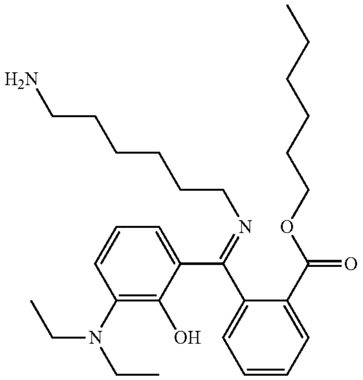
And
-continued
Imine-10
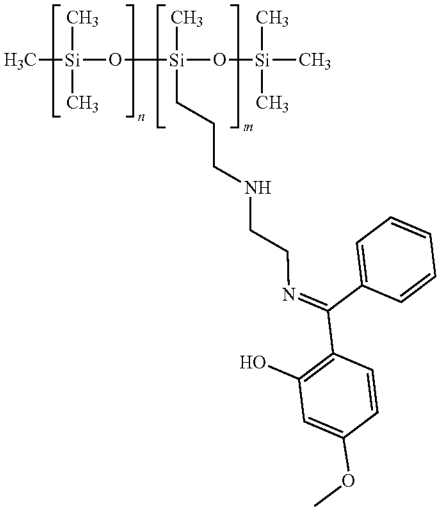
.
4. A cosmetic or pharmaceutical preparation comprising the sunscreen active ingredient of claim 3 and a cosmetically or pharmaceutically acceptable carrier.
* * * * *